(12) United States Patent
Cai

(10) Patent No.: US 11,376,290 B2
(45) Date of Patent: Jul. 5, 2022

(54) RECOMBINANT ONCOLYTIC VIRUS, SYNTHETIC DNA SEQUENCE, AND APPLICATION THEREOF

(71) Applicant: Wuhan Boweid Biotechnology Co., Ltd., Wuhan (CN)

(72) Inventor: Ligang Cai, Wuhan (CN)

(73) Assignee: WUHAN BOWEID BIOTECHNOLOGY CO., LTD., Wuhan (CN)

( * ) Notice: Subject to any disclaimer, the term of this patent is extended or adjusted under 35 U.S.C. 154(b) by 301 days.

(21) Appl. No.: 16/528,689

(22) Filed: Aug. 1, 2019

(65) Prior Publication Data

US 2019/0350993 A1 Nov. 21, 2019

Related U.S. Application Data

(63) Continuation-in-part of application No. 16/352,806, filed on Mar. 13, 2019, which is a continuation-in-part of application No. 62/643,166, filed on Mar. 14, 2018.

(51) Int. Cl.
| | |
|---|---|
| *A61K 35/763* | (2015.01) |
| *C12N 15/86* | (2006.01) |
| *C07K 14/705* | (2006.01) |
| *A61K 9/00* | (2006.01) |
| *A61P 35/00* | (2006.01) |

(52) U.S. Cl.
CPC .......... *A61K 35/763* (2013.01); *A61K 9/0017* (2013.01); *A61P 35/00* (2018.01); *C07K 14/70532* (2013.01); *C07K 14/70596* (2013.01); *C12N 15/86* (2013.01)

(58) Field of Classification Search
CPC .................................................. A61K 35/763
See application file for complete search history.

(56) References Cited

U.S. PATENT DOCUMENTS 9,617,344 B2 * 4/2017 Lee .................... C07K 16/2863

OTHER PUBLICATIONS

Fountzilas et al. (Oncotarget, 2017, vol. 8, (No. 60), pp. 102617-102639). (Year: 2017).*
Ma et al. (Dig Dis Sci (2009) 54:1425-1431) (Year: 2009).*
Zhang et al. (Cell. Sep. 6, 2018; 174(6): 1465-1476.e13.) (Year: 2018).*
Massilamany et al. (PLOS ONE | DOI:10.1371/journal.pone.0131052 Jun. 22, 2015). (Year: 2015).*

* cited by examiner

*Primary Examiner* — Scott Long
(74) *Attorney, Agent, or Firm* — Matthias Scholl P.C.; Matthias Scholl

(57) ABSTRACT

A recombinant oncolytic virus, a synthetic DNA sequence and applications of the virus. The recombinant oncolytic virus includes a genome and an exogenous DNA sequence inserted in the genome. The exogenous DNA sequence adapts to express a basic peptide fragment, to increase the environmental pH in a host infected by the recombinant oncolytic virus. More than 60% of amino acids in the basic peptide fragment are basic amino acids. The recombinant oncolytic virus and the synthetic DNA sequence of the disclosure are used to prepare an anti-tumor drug.

6 Claims, 16 Drawing Sheets

Specification includes a Sequence Listing.

CVB3 Nancy strain

Recombinant CVB3

Negative control group

Example 14

Example 5

FIG. 12

A. Vero cells (negative control) before being stained
B. Vero cells (negative control) after being stained
C. 9pep group before being stained   D. 9pep group after being stained
E. 4p5 group before being stained    F. 4p5 group after being stained

RECOMBINANT ONCOLYTIC VIRUS, SYNTHETIC DNA SEQUENCE, AND APPLICATION THEREOF

CROSS-REFERENCE TO RELATED APPLICATIONS

This application is a continuation-in-part of U.S. Ser. No. 16/352,806 filed Mar. 13, 2019, now pending, which is a continuation-in-part of U.S. Provisional Application No. 62643166 filed Mar. 14, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a recombinant oncolytic virus, a synthetic DNA sequence, and application thereof.

Oncolytic viruses are viruses that preferentially infect and kill cancer cells. Wild-type oncolytic viruses are toxic. When an organism is infected with a wild-type oncolytic virus, systemic symptoms such as fever and chills occur.

SUMMARY

Disclosed is a recombinant oncolytic virus, a synthetic DNA sequence, and methods of using the same. The disclosure aims at inhibiting tumor cells by providing a recombinant oncolytic virus capable of modifying the microenvironment of the tumor.

To achieve the above objective, according to one embodiment of the invention, there is provided a recombinant oncolytic virus, comprising: an oncolytic virus genome and an exogenous DNA sequence inserted in the oncolytic virus genome, the exogenous DNA sequence being adapted to express a basic peptide fragment, to increase environmental pH in a host infected by the recombinant oncolytic virus.

The oncolytic virus genome can be a genome of herpes virus, Coxsackie viruses, adenovirus, cowpox virus, measles virus, poliomyelitis virus, retroviruses, reovirus, respiratory syncytial virus, parvovirus H1, vesicular stomatitis virus, or Newcastle disease virus, and preferably adenovirus, Newcastle disease virus, or Coxsackie virus.

The environmental pH in the host infected by the recombinant oncolytic virus can be increased by 0.4 to 0.6.

The basic peptide fragment can comprise 4 to 10 amino acids.

More than 60% of amino acids in the basic peptide fragment are basic amino acids.

More than 80% of amino acids in the basic peptide fragment are basic amino acids.

The basic amino acids can be selected from Arginine, Lysine, and Histidine.

The basic amino acids can be selected from Arginine and Lysine.

The basic peptide fragment can be selected from:

```
                                          (SEQ ID NO: 3)
Arg-Lys-Arg-Lys;

(SEQ ID NO: 5)
Lys-Arg-Lys-Arg;

(SEQ ID NO: 7)
Arg-Arg-Lys-Lys;

(SEQ ID NO: 9)
Lys-Lys-Arg-Arg;

(SEQ ID NO: 11)
Lys-Arg-Arg-Lys;

(SEQ ID NO: 13)
Arg-Lys-Lys-Arg;

(SEQ ID NO: 15)
Arg-Arg-His-Lys-Lys;

(SEQ ID NO: 17)
Lys-His-Arg-Lys-His-Arg;

(SEQ ID NO: 19)
Lys-His-Arg-Cys-Lys-Pro;

(SEQ ID NO: 21)
Arg-Arg-His-Lys-Met-Lys;

(SEQ ID NO: 23)
His-Arg-Lys-Cys-Arg-Lys;

(SEQ ID NO: 25)
Lys-Arg-Trp-Arg-Lys-His-Arg;

(SEQ ID NO: 27)
His-Lys-Gly-Arg-Lys-Cys-Arg-Val;

(SEQ ID NO: 29)
Lys-Arg-Trp-His-Lys-Met-Arg-Lys-His;

(SEQ ID NO: 31)
His-Phe-Trp-Arg-Gln-Cys-Ala-Met-Lys;

(SEQ ID NO: 33)
Tyr-Phe-Pro-Arg-His-Gln-Lys-Trp-Lys;

(SEQ ID NO: 35)
Trp-Lys-Tyr-Arg-Gln-Ile-Ser-Thr-Cys;
and (SEQ ID NO: 37)
Arg-Lys-His-Lys-Met-Arg-Lys-Cys-His-Lys.
```

With regard to the recombinant oncolytic virus, the recombinant oncolytic virus can be Coxsackie virus B3 strain.

With regard to the recombinant oncolytic virus, the basic peptide fragment can be selected from:

```
                                          (SEQ ID NO: 11)
Lys-Arg-Arg-Lys;

(SEQ ID NO: 29)
Lys-Arg-Trp-His-Lys-Met-Arg-Lys-His;
and (SEQ ID NO: 31)
His-Phe-Trp-Arg-Gln-Cys-Ala-Met-Lys.
```

With regard to the recombinant oncolytic virus, the recombinant oncolytic virus can be a variant attenuated Coxsackie virus B3 strain comprising base mutations of T97C, G1180A, T1654C, T1756C, G2276A, A2685C, G2690A, C3120A, A3231G, G4327A, T5088C, A5270G, C7026T, and/or G7192A.

The exogenous DNA sequence can be inserted onto a pVAX1 vector.

With regard to the recombinant oncolytic virus, the basic peptide fragment can be Lys-Arg-Trp-His-Lys-Met-Arg-Lys-His (SEQ ID NO: 29).

According to another aspect of the disclosure, the disclosure provides an application of the abovementioned recombinant oncolytic virus for preparation of an anti-tumor drug.

The anti-tumor drug can be an anti-solid tumor drug.

The anti-solid tumor drug can be used for treating respiratory tract tumors, gastrointestinal tumors, endocrine tumors, or gynecological tumors.

According to another aspect of the disclosure, an anti-tumor drug is provided, which comprises the recombinant oncolytic virus provided in the disclosure.

The anti-tumor drug can further comprise a checkpoint inhibitor.

According to another aspect of the disclosure, there provided is a method for treating a malignant tumor, the method comprising administering the anti-tumor drug intravenously or locally to a patient in need thereof.

The malignant tumor can be a solid tumor.

The malignant tumor can be respiratory tract tumor, gastrointestinal tumor, endocrine tumor, or gynecological tumor.

According to another aspect of the disclosure, a synthetic DNA sequence is provided, which is adapted to express a basic peptide fragment comprising basic amino acids at a content of more than 60%.

With regard to the synthetic DNA sequence, the basic peptide fragment can comprise basic amino acids at a content of more than 80%.

The basic amino acids can be selected from Arginine, Lysine, and Histidine.

With regard to the synthetic DNA sequence, the basic peptide fragment can be selected from:

```
                                          (SEQ ID NO: 3)
Arg-Lys-Arg-Lys;

(SEQ ID NO: 5)
Lys-Arg-Lys-Arg;

(SEQ ID NO: 7)
Arg-Arg-Lys-Lys;

(SEQ ID NO: 9)
Lys-Lys-Arg-Arg;

(SEQ ID NO: 11)
Lys-Arg-Arg-Lys;

(SEQ ID NO: 13)
Arg-Lys-Lys-Arg;

(SEQ ID NO: 15)
Arg-Arg-His-Lys-Lys;

(SEQ ID NO: 17)
Lys-His-Arg-Lys-His-Arg;

(SEQ ID NO: 19)
Lys-His-Arg-Cys-Lys-Pro;

(SEQ ID NO: 21)
Arg-Arg-His-Lys-Met-Lys;

(SEQ ID NO: 23)
His-Arg-Lys-Cys-Arg-Lys;

(SEQ ID NO: 25)
Lys-Arg-Trp-Arg-Lys-His-Arg;

(SEQ ID NO: 27)
His-Lys-Gly-Arg-Lys-Cys-Arg-Val;

(SEQ ID NO: 29)
Lys-Arg-Trp-His-Lys-Met-Arg-Lys-His;
```

```
                                          (SEQ ID NO: 31)
His-Phe-Trp-Arg-Gln-Cys-Ala-Met-Lys;

(SEQ ID NO: 33)
Tyr-Phe-Pro-Arg-His-Gln-Lys-Trp-Lys;

(SEQ ID NO: 35)
Trp-Lys-Tyr-Arg-Gln-Ile-Ser-Thr-Cys;
and (SEQ ID NO: 37)
Arg-Lys-His-Lys-Met-Arg-Lys-Cys-His-Lys.
```

With regard to the synthetic DNA sequence, the basic peptide fragment can be selected from:

```
                                          (SEQ ID NO: 11)
Lys-Arg-Arg-Lys;

(SEQ ID NO: 29)
Lys-Arg-Trp-His-Lys-Met-Arg-Lys-His;
and (SEQ ID NO: 31)
His-Phe-Trp-Arg-Gln-Cys-Ala-Met-Lys.
```

Advantages of the embodiments of the disclosure include:

(1) The recombinant oncolytic virus provided in the disclosure modifies the interstitial pH in the tumor focus, so as to affect the microenvironment where the tumor cells grow and inhibit the tumor growth. The recombinant oncolytic virus has a broad-spectrum anti-tumor effect and has good application prospects when used during preparation of anti-tumor drugs. The recombinant oncolytic virus acts on the microenvironment where the tumor grows instead of the tumor cells themselves. The recombinant oncolytic virus proliferates with the proliferation of the malignant tumor cells and continuously express the basic polypeptide, so the anti-tumor effect is cumulative and automatically adapts to the development of the tumors without over-treatment.

In a preferred embodiment, the recombinant oncolytic virus provided in the disclosure may be obtained from various known oncolytic viruses. Because the expression of the basic peptide fragment acts on the cellular microenvironment, which does not conflict with the mechanisms of action of recombinant oncolytic viruses that express specific genes killing or inhibiting tumor cells, the inhibition effects are mutually beneficial to each other, and the anti-tumor effect is significant.

For example, Coxsackie CVB 3 is used in combination with a gene expressing a 4-peptide or 9-peptide fragment having lysine at the N-terminus, which can modify the interstitial acid-base environment in the tumor focus and has excellent anti-solid tumor effect. Moreover, the toxicity is low, and the adverse effect is small, causing only a mild fever response. In addition, Coxsackie virus is an RNA virus, which will not integrate into the host cells and causes no risk of transcription.

(2) The compositions for treating tumors provided in the disclosure are suitable for intravenous administration due to their safety, precision of targeting, high specificity, and low toxicity.

(3) The exogenous DNA sequence encoding the basic peptide fragment provided in the disclosure expresses the basic peptide fragment to change the pH in a cellular microenvironment and inhibits the growth of tumor cells.

BRIEF DESCRIPTION OF THE DRAWINGS

FIG. 12 shows SEM images of myocardial tissue sections of BALB/C mice taken after 6 days of toxicity test in Example 25 of the disclosure;

DETAILED DESCRIPTION OF THE EMBODIMENTS

Figure 1:
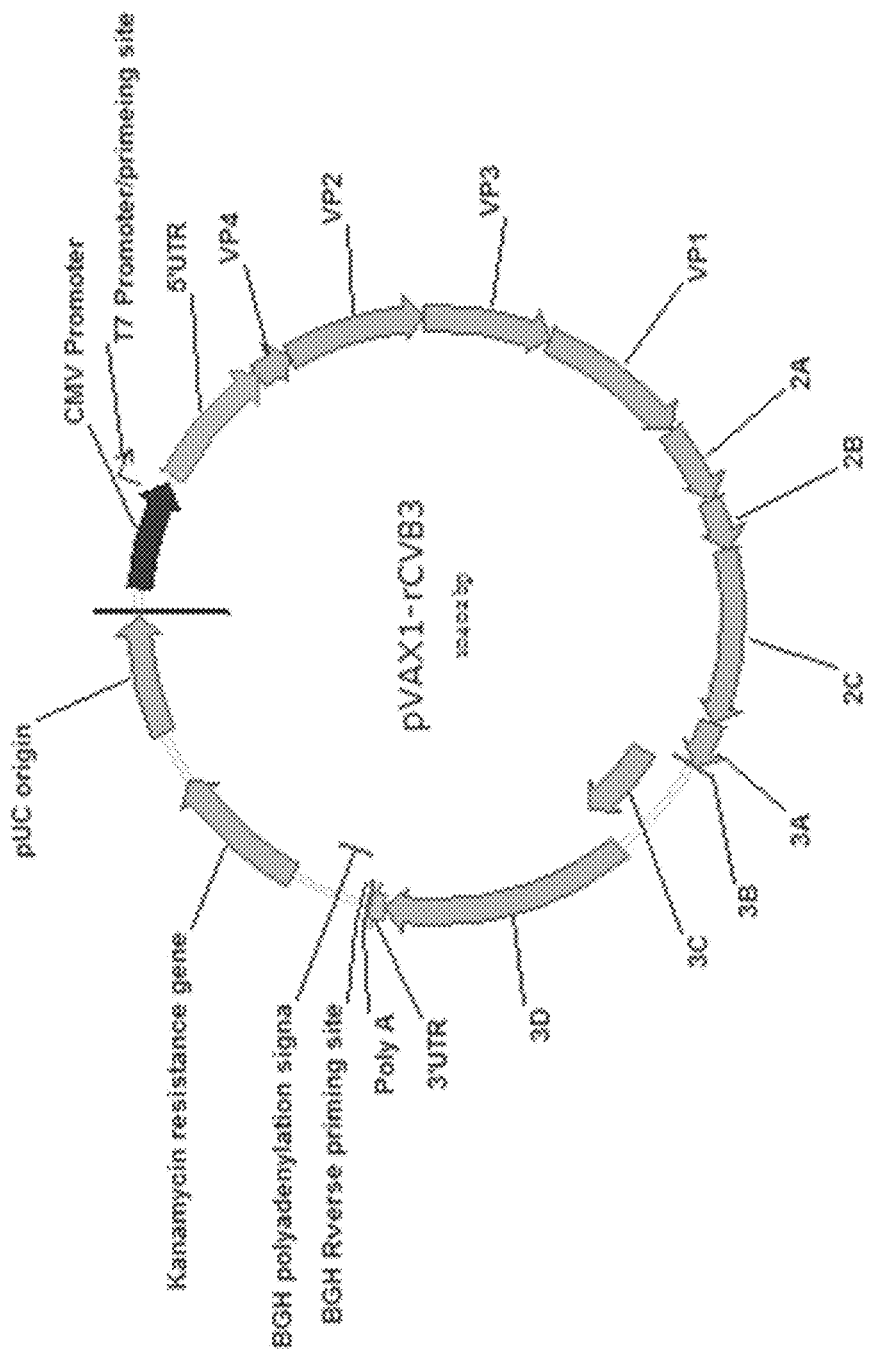
FIG. 1 is a schematic gene map of Coxsackie virus carrying a eukaryotic expression vector pVAX1 provided in an example of the disclosure.

For further illustrating the invention, experiments detailing a recombinant oncolytic virus, a basic peptide fragment and applications thereof are described below.

The disclosure provides a recombinant oncolytic virus, which comprises an exogenous DNA sequence inserted in its genome, and expresses the basic peptide fragment in a physiological process, such that the environmental pH in a host infected therewith is increased by 0.4 to 0.6. After infection with the recombinant oncolytic virus comprising the exogenous gene, the basic peptide fragment is highly expressed thus changing the microenvironment of the tumor tissue, such that the tumor tissues are inhibited and killed.

The recombinant oncolytic virus can be herpes viruses, Coxsackie viruses, adenovirus, cowpox virus, measles virus, poliomyelitis virus, retroviruses, reovirus, respiratory syncytial virus, parvovirus H1, vesicular stomatitis virus, or Newcastle disease virus. The recombinant oncolytic virus is preferably recombinant oncolytic viruses that deactivate or delete specific genes in the target cells, for example, adenovirus, Newcastle disease virus or Coxsackie viruses.

The basic peptide fragment comprises 4 to 10 amino acids, in which the basic amino acids account for more than 60%, and preferably more than 80%, The basic amino acids are selected from Arginine, Lysine, or Histidine, and preferably from Arginine or Lysine. The basic peptide fragment has an N-terminal amino acid that is Lysine optimally.

The basic peptide fragment is selected from:

```
                                          (SEQ ID NO: 3)
    Arg-Lys-Arg-Lys;

(SEQ ID NO: 5)
    Lys-Arg-Lys-Arg;

(SEQ ID NO: 7)
    Arg-Arg-Lys-Lys;

(SEQ ID NO: 9)
    Lys-Lys-Arg-Arg;

(SEQ ID NO: 11)
    Lys-Arg-Arg-Lys;

(SEQ ID NO: 13)
    Arg-Lys-Lys-Arg;

(SEQ ID NO: 15)
    Arg-Arg-His-Lys-Lys;

(SEQ ID NO: 17)
    Lys-His-Arg-Lys-His-Arg;

(SEQ ID NO: 19)
    Lys-His-Arg-Cys-Lys-Pro;

(SEQ ID NO: 21)
    Arg-Arg-His-Lys-Met-Lys;

(SEQ ID NO: 23)
    His-Arg-Lys-Cys-Arg-Lys;

(SEQ ID NO: 25)
    Lys-Arg-Trp-Arg-Lys-His-Arg;

(SEQ ID NO: 27)
    His-Lys-Gly-Arg-Lys-Cys-Arg-Val;

(SEQ ID NO: 29)
    Lys-Arg-Trp-His-Lys-Met-Arg-Lys-His;

(SEQ ID NO: 31)
    His-Phe-Trp-Arg-Gln-Cys-Ala-Met-Lys;

(SEQ ID NO: 33)
    Tyr-Phe-Pro-Arg-His-Gln-Lys-Trp-Lys;

(SEQ ID NO: 35)
    Trp-Lys-Tyr-Arg-Gln-Ile-Ser-Thr-Cys;
    and (SEQ ID NO: 37)
    Arg-Lys-His-Lys-Met-Arg-Lys-Cys-His-Lys.
```

In a preferred embodiment, Coxsackie virus, particularly an attenuated variant strain of Coxsackie virus is used. In a pVAX1 vector constructed to have the viral genome, a gene is inserted that expresses a basic peptide fragment selected from:

```
                                          (SEQ ID NO: 5)
    Lys-Arg-Lys-Arg;

(SEQ ID NO: 29)
    Lys-Arg-Trp-His-Lys-Met-Arg-Lys-His;
    and (SEQ ID NO: 31)
    His-Phe-Trp-Arg-Gln-Cys-Ala-Met-Lys.
```

In a further preferred embodiment, the basic peptide fragment is selected from

```
                                          (SEQ ID NO: 11)
Lys-Arg-Arg-Lys;
and (SEQ ID NO: 29)
Lys-Arg-Trp-His-Lys-Met-Arg-Lys-His.
```

Figure 2:
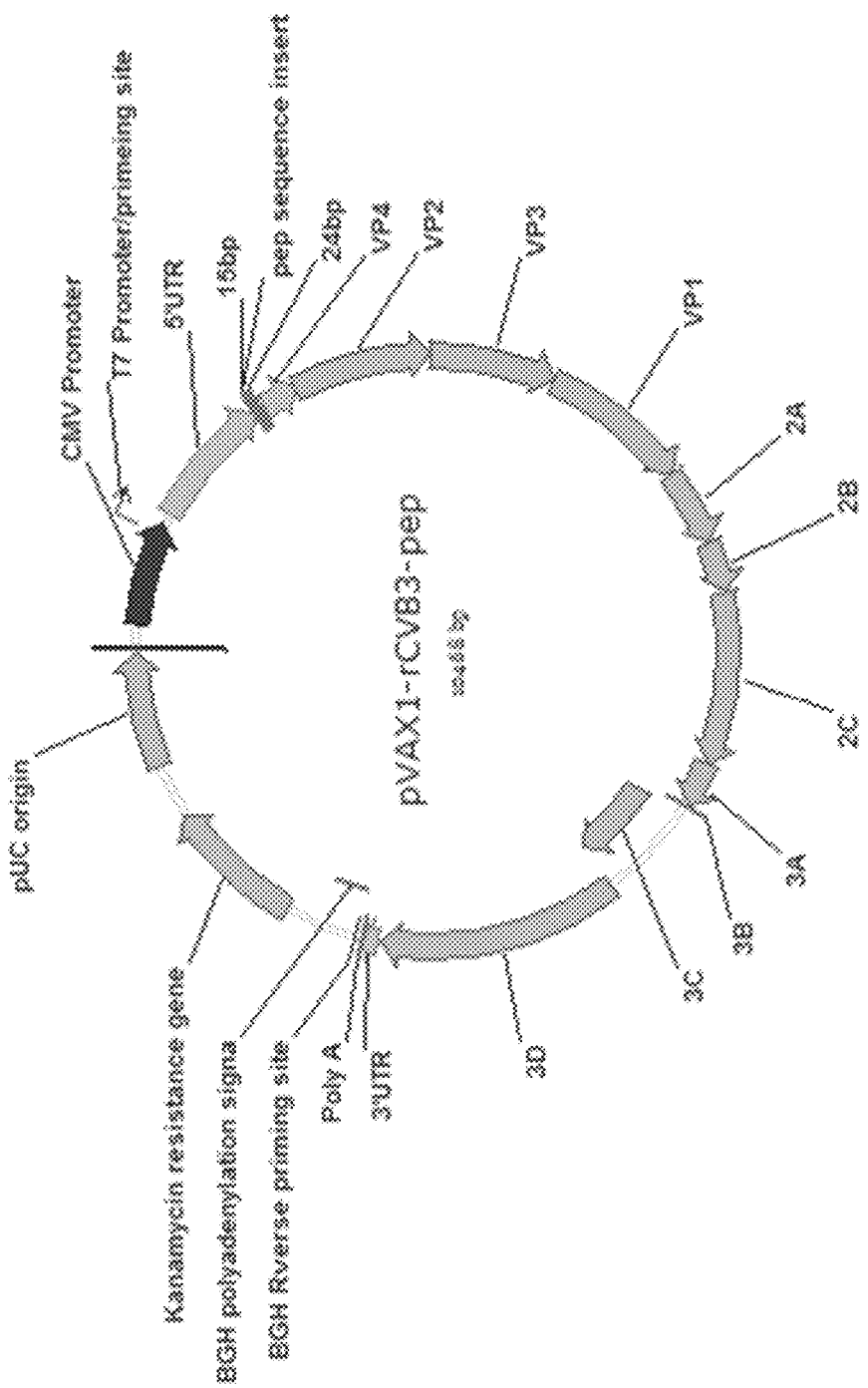
FIG. 2 is a schematic gene map of Coxsackie virus carrying a eukaryotic expression vector pVAX1 in which a synthetic DNA sequence is inserted provided in an example of the disclosure.

When the Coxsackie virus CVB 3 strain is used, the exogenous peptide fragment is Lys-Arg-Trp-His-Lys-Met-Arg-Lys-His (SEQ ID NO: 29), so excellent tumor inhibition effect and good safety are exhibited.

The Coxsackie virus CVB 3 is preferably the variant attenuated Coxsackie virus B3 strain comprising base mutations of T97C, G1180A, T1654C, T1756C, G2276A, A2685C, G2690A, C3120A, A3231G, G4327A, T5088C, A5270G, C7026T, and/or G7192A. The sequence encoding the basic peptide fragment is inserted onto the pVAX1 vector.

The DNA sequence encoding the basic peptide fragment is inserted between the 5'UTR and VP4 of the recombinant vector.

Application of the recombinant oncolytic virus provided in the disclosure in the preparation of anti-tumor drug, particularly anti-solid tumor drugs, for examples, drugs for treating respiratory tract tumors, gastrointestinal tumors, endocrine tumors, or gynecological tumors, is further provided in the disclosure. The recombinant oncolytic virus provided in the invention, upon reaching the focal area, express the basic peptide fragment by making use of the targeting and replication ability of the virus, based on the severity of the tumor. It is experimentally confirmed that the basic peptide fragment changes the pH in the microenvironment where tumor cells resides, including the intracellular and intercellular environment. This change brings a series of comprehensive impacts on the metabolism of tumor cells, and finally results in an obvious tumor suppression effect. Therefore, the existing recombinant oncolytic viruses, in theory, can be genetically modified to carry the exogenous synthetic DNA sequence, so that in addition to the original inhibition on or killing of tumor cells, an inhibitory effect is produced by changing the microenvironment where the tumor cells grow. The two effects are synergistic, so as to inhibit the tumor more effectively. The recombinant oncolytic virus provided in the disclosure exerts an anti-tumor effect by impacting the microenvironment where the tumor cells grow, and thus has a more pronounced inhibitory effect on the solid tumor in which the tumor cells are concentrated. At the same time, for the recombinant oncolytic virus that causes serious physiological reaction, the dosage and dosage range of the virus used is reduced due to the superimposed tumor suppressive effect, so the physiological adverse effect resulting therefrom is lowered, the application of the recombinant oncolytic virus is widened and the safety of the recombinant oncolytic virus is improved.

The disclosure provides an anti-tumor drug, which comprises the recombinant oncolytic virus provided in the disclosure. Preferably, the anti-tumor drug further comprises an immune checkpoint inhibitor. The drug is administered intravenously or topically to the focus, thus exerting a good tumor suppressive effect. The immune checkpoint inhibitor (PD-1, PD-L1, and CTLA4) is not highly responsive to solid tumors (except melanoma), possibly due to the insufficient stimulation to the immune system in the patients with solid tumors after the release of the immune system by the checkpoint inhibitor. In the disclosure, the recombinant oncolytic virus and the immune checkpoint inhibitor synergize, thereby significantly enhancing the killing effect of the immune system for solid tumors, increasing the local infiltration of immune cells into the tumors, and up-regulating PD-L1. Particularly, the recombinant CVB3 virus induces the local production of specific and nonspecific immune responses in the tumor, such as exposure of calreticulin (CRT), translocation of ATP, and intracellular translocation of HGMB1 (Extracellular High Mobility Group Box 1). As the recombinant oncolytic virus proliferates, the IFN and/or cytokines are induced to produce activated NK and DC cells, whereby various mature DCs and cytotoxic CD107a+ NK cells are facilitate to enter the tumor site, resulting in the changes in the immune cellular profile in the tumor microenvironment and thus restoring the inherent antitumor immunity of an organism. The synergistic effect between the recombinant Coxsackie virus and the immune checkpoint inhibitor provided in the disclosure is particularly obvious.

The disclosure further provides a synthetic DNA sequence that expresses a basic peptide fragment. The basic amino acid in the basic peptide fragment has a content of more than 60% and preferably more than 80%. The basic amino acid is selected from Arginine, Lysine or Histidine, and preferably from Arginine or Lysine. The basic peptide fragment preferably has a N-terminal amino acid that is Lysine.

The basic peptide fragment encoded by the synthetic DNA sequence is elected from:

```
                                          (SEQ ID NO: 3)
Arg-Lys-Arg-Lys;

(SEQ ID NO: 5)
Lys-Arg-Lys-Arg;

(SEQ ID NO: 7)
Arg-Arg-Lys-Lys;

(SEQ ID NO: 9)
Lys-Lys-Arg-Arg;

(SEQ ID NO: 11)
Lys-Arg-Arg-Lys;

(SEQ ID NO: 13)
Arg-Lys-Lys-Arg;

(SEQ ID NO: 15)
Arg-Arg-His-Lys-Lys;

(SEQ ID NO: 17)
Lys-His-Arg-Lys-His-Arg;

(SEQ ID NO: 19)
Lys-His-Arg-Cys-Lys-Pro;

(SEQ ID NO: 21)
Arg-Arg-His-Lys-Met-Lys;

(SEQ ID NO: 23)
His-Arg-Lys-Cys-Arg-Lys;

(SEQ ID NO: 25)
Lys-Arg-Trp-Arg-Lys-His-Arg;

(SEQ ID NO: 27)
His-Lys-Gly-Arg-Lys-Cys-Arg-Val;
```

(SEQ ID NO: 29)
Lys-Arg-Trp-His-Lys-Met-Arg-Lys-His;

(SEQ ID NO: 31)
His-Phe-Trp-Arg-Gln-Cys-Ala-Met-Lys;

The recombinant oncolytic virus provided in this example comprises the exogenous synthetic DNA sequence inserted between the 5'UTR and VP4 of the constructed recombinant vector by a reverse genetic method. A 15 bp (SEQ ID NO: 1) and a 24 bp (SEQ ID NO: 2) DNA sequence are located at respectively the 5' and the 3' terminus of the sequence, which are provided for recognition and cleavage by the Protease C, as shown in FIG. 2.

TABLE 1

Basic peptide fragments and Its Encoding Genes

| Example | Polypeptide name | Polypeptide sequence | Gene name | Gene sequence |
|---|---|---|---|---|
| 1 | Polypeptide 1 | SEQ ID NO: 3 | nucleotide seque 1 | SEQ ID NO: 4 |
| 2 | Polypeptide 2 | SEQ ID NO: 5 | nucleotide seque 2 | SEQ ID NO: 6 |
| 3 | Polypeptide 3 | SEQ ID NO: 7 | nucleotide seque 3 | SEQ ID NO: 8 |
| 4 | Polypeptide 4 | SEQ ID NO: 9 | nucleotide seque 4 | SEQ ID NO: 10 |
| 5 | Polypeptide 5 | SEQ ID NO: 11 | nucleotide seque 5 | SEQ ID NO: 12 |
| 6 | Polypeptide 6 | SEQ ID NO: 13 | nucleotide seque 6 | SEQ ID NO: 14 |
| 7 | Polypeptide 7 | SEQ ID NO: 15 | nucleotide seque 7 | SEQ ID NO: 16 |
| 8 | Polypeptide 8 | SEQ ID NO: 17 | nucleotide seque 8 | SEQ ID NO: 18 |
| 9 | Polypeptide 9 | SEQ ID NO: 19 | nucleotide seque 9 | SEQ ID NO: 20 |
| 10 | Polypeptide 10 | SEQ ID NO: 21 | nucleotide seque 10 | SEQ ID NO: 22 |
| 11 | Polypeptide 11 | SEQ ID NO: 23 | nucleotide seque 11 | SEQ ID NO: 24 |
| 12 | Polypeptide 12 | SEQ ID NO: 25 | nucleotide seque 12 | SEQ ID NO: 26 |
| 13 | Polypeptide 13 | SEQ ID NO: 27 | nucleotide seque 13 | SEQ ID NO: 28 |
| 14 | Polypeptide 14 | SEQ ID NO: 29 | nucleotide seque 14 | SEQ ID NO: 30 |
| 15 | Polypeptide 15 | SEQ ID NO: 31 | nucleotide seque 15 | SEQ ID NO: 32 |
| 16 | Polypeptide 16 | SEQ ID NO: 33 | nucleotide seque 16 | SEQ ID NO: 34 |
| 17 | Polypeptide 17 | SEQ ID NO: 35 | nucleotide seque 17 | SEQ ID NO: 36 |
| 18 | Polypeptide 18 | SEQ ID NO: 37 | nucleotide seque 18 | SEQ ID NO: 38 |

(SEQ ID NO: 33)
Tyr-Phe-Pro-Arg-His-Gln-Lys-Trp-Lys;

(SEQ ID NO: 35)
Trp-Lys-Tyr-Arg-Gln-Ile-Ser-Thr-Cys;
and (SEQ ID NO: 37)
Arg-Lys-His-Lys-Met-Arg-Lys-Cys-His-Lys.

The basic peptide fragment preferably has a sequence of:

(SEQ ID NO: 11)
Lys-Arg-Arg-Lys;

(SEQ ID NO: 29)
Lys-Arg-Trp-His-Lys-Met-Arg-Lys-His;
and (SEQ ID NO: 31)
His-Phe-Trp-Arg-Gln-Cys-Ala-Met-Lys.

Examples 1 to 18

Recombinant Coxsackie Viruses Having a Synthetic DNA Sequence Inserted in their Genome The whole genome sequence of the Coxsackie B3 Nancy strain is as shown in GeneBank II): JX312064.1. The recombinant Coxsackie virus strain comprises the base mutations of T97C, G1180A, T1654C, T1756C, G2276A, A2685C, G2690A, C3120A, A3231G, G4327A, T5088C, A5270G, C7026T, and G7192A. The complete cDNA sequence of the recombinant Coxsackie virus strain is synthesized by Wuhan Boweid Biotechnology Co., Ltd and constructed onto a eukaryotic expression vector pVAX1 by a molecular biological method, as shown in FIG. 1.

The sequence is specifically inserted by inserting the basic peptide fragment expressing DNA sequence between the 5'UTR and VP4 of the recombinant vector. After screening, a positive clone is obtained, which is sequenced and extracted for the plasmid, to obtain a complete cDNA for viral packaging.

This example was specifically as follows.

(1) Synthesis of Coxsackie virus gene CVB3-Am pUC57-CVB3-Am was synthesized by Suzhou Genwiz Biotechnology Co., Ltd.

(2) Mini extraction of vector pVAX1 and pUC19

The pVAX1-SalI and pUC19 plasmids were extracted from Stbl3 using the kit Axygen, Cat. No: AP-MN-P-250 available from Axygen.

(3) Construction of pVAX1-SalI-CVB3-Am vector a. Double cleavage and recovery

The plasmids pVAX1 (Apa I→Sal I) and pUC57-CVB3-Am were cleaved with both Not I and Sal I, and subjected to 1% agarose gel electrophoresis after reaction. The vector of 2999 bp and the CVB3-Am fragment of about 7500 bp were recovered, followed by gel extraction. The purification of the cleaved products was carried out following the specific steps as described in instructions for the Gel Extraction Kit from Axygen.

b. Ligation and Transformation

The CVB3-Am fragment and the vector pVAX1(Apa I→Sal I) that were cleaved with both Not I and Sal I were ligated at a ratio by the T4DNA ligase available from TAKARA, and then transformed into Stbl3 chemically competent cell.

c. Screening and Identification of Positive Clones

Single colonies grown on a LB+Kana plate were randomly picked up and subjected to colony PCR. The correct positive clones were sequenced.

The pVAX1 vector carrying the complete cDNA sequence of the recombinant Coxsackie virus was transfected into Cos 7 packaging cells. The cells were cultured to obtain an infectious recombinant virus suspension.

A PolyA sequence ranging from 20 to 100 bp and preferably from 30 to 80 bp in length were preferably inserted after the 3'UTR, to effectively ensure the stability of the basic peptide fragment encoding gene, thereby ensuring the expression thereof. The virus can be stored at −20° C. for over 1 year, and at room temperature for 2 days without decline of the titer. Therefore, the virus is highly stable, and convenient in storage and transportation.

Comparative Example 1: The synthetic DNA sequence was inserted between the VP1 and 2A elements in the pVAX1 vector to obtain the virus. The virus could not stably express the basic peptide fragment and had a limited inhibitory effect on cancer cells.

Example 19

Preparation of Test Samples for Pharmacodynamics Study

Figure 3:
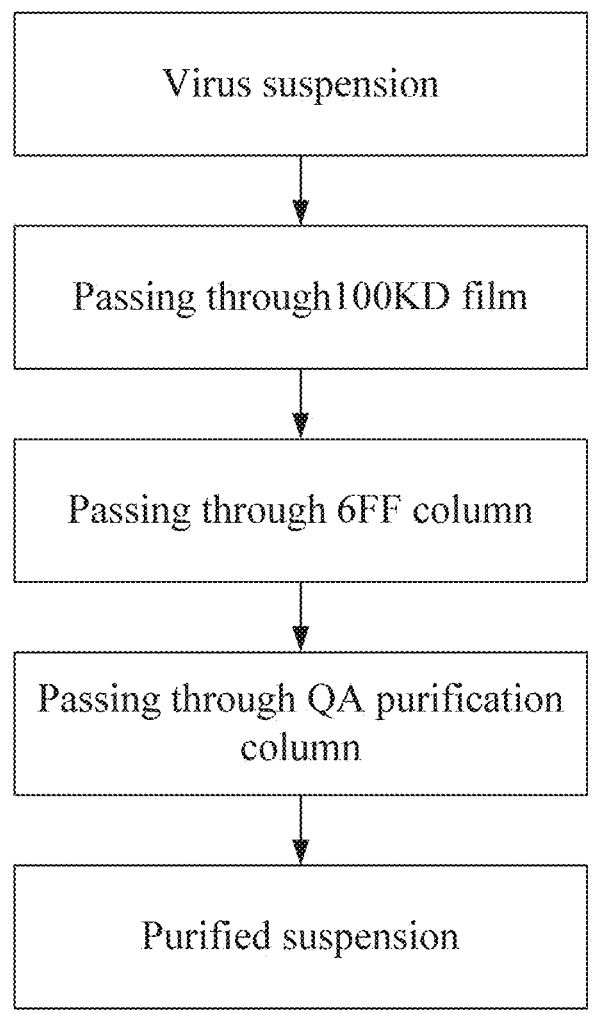
FIG. 3 is a simplified process chart of virus purification provided in an example of the disclosure.

The infectious recombinant virus suspension described in Examples 1 to 18 was inoculated to the expansion cultured Vero cells, and a purified virus suspension was obtained after the production and purification processes, which was used as a test sample. The process for virus purification was as shown in FIG. 3.

The purified virus suspension needs to be inspected to satisfy the following criteria as shown in Table 2.

TABLE 2

| Item of inspection | Method | Standard limit released |
|---|---|---|
| Protein content | Chinese Pharmacopoeia 2015 Edition, Part VI, General rule 0731 Protein Determination Method V: Bradford method. | ≤1 µg/dose |
| Virus titer | TCID50 Karber method | ≥$10^7$ $TCID_{50}$/mL |

Example 20

In Vivo Pharmacodynamics Study on the Selective Inhibition of Recombinant Coxsackie Virus on Solid Tumors The test samples used in this example were prepared and tested according to the protocol described in Example 19.

In this example, the recombinant Coxsackie viruses of Examples 1 to 18 were used as test samples, for example, those prepared in Example 5, Example 14, and Example 17.

The viruses above were prepared into test samples following the method as described in Example 19.

A subcutaneous A549 cell transplanted tumor model of lung cancer in nude mice was established. 30 tumor-bearing animals having uniform tumor volume were screened. The 30 animals with a tumor volume of 45-70 mm$^3$ (average tumor volume of 56 mm$^3$) were assigned to Groups 1-5 at random. Each group of animals were randomly numbered using Excel software and ranked according to the random number from small to large. There were a total of 5 groups, each group having 6 animals. The groups, dosage and administration mode are shown in Table 3.

TABLE 3

| Group | Agent administered to the animals | Dosage (PFU/kg) | Concentration (PFU/mL) | Administration mode | Volume dosed |
|---|---|---|---|---|---|
| 1 | Saline (negative) | 0.1 mL/10 g | — | Intravenous injection | 0.1 mL/10 g |
| 2 | Cisplatin (positive) | 6 mg/kg | 0.6 mg/mL | Intravenous injection | 0.1 mL/10 g |
| 3 | Example 5 | $6 \times 10^6$ | $6 \times 10^4$ | Intravenous injection | 0.1 mL/10 g |
| 4 | Example 14 | $6 \times 10^5$ | $6 \times 10^3$ | Intravenous injection | 0.1 mL/10 g |
| 5 | Example 17 | $6 \times 10^4$ | $6 \times 10^2$ | Intravenous injection | 0.1 mL/10 g |

The animals in Group 2 (Cisplatin) were administered once a week for 4 consecutive weeks. After 1-week observation, the animals were euthanized on Day 41. In the saline group, the animals were administered with saline once a week for 6 consecutive weeks, and the animals were euthanized on Day 41. The animals were observed twice a day during administration to observe the general clinical symptoms of animals, and the body weight and tumor size were measured twice a week.

Figure 4:
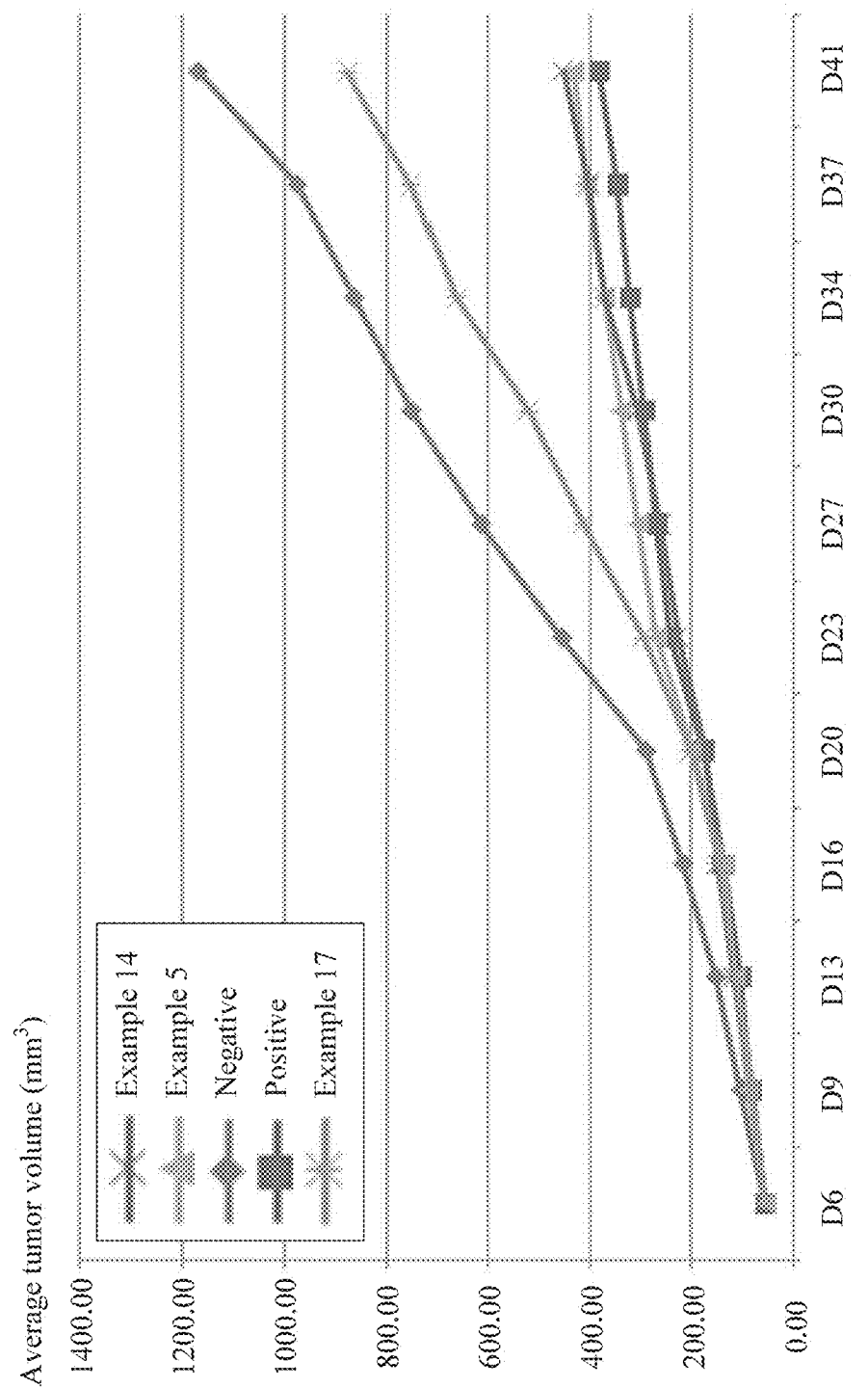
FIG. 4 is a tumor volume curve provided in Example 20 of the disclosure.

Results: Throughout the experiment, the average body weight of the animals is increased, and there is no significant difference between groups (P<0.05). The curve of increase in average tumor volume of the animals in each group with time is shown in FIG. 4.

Figure 5:
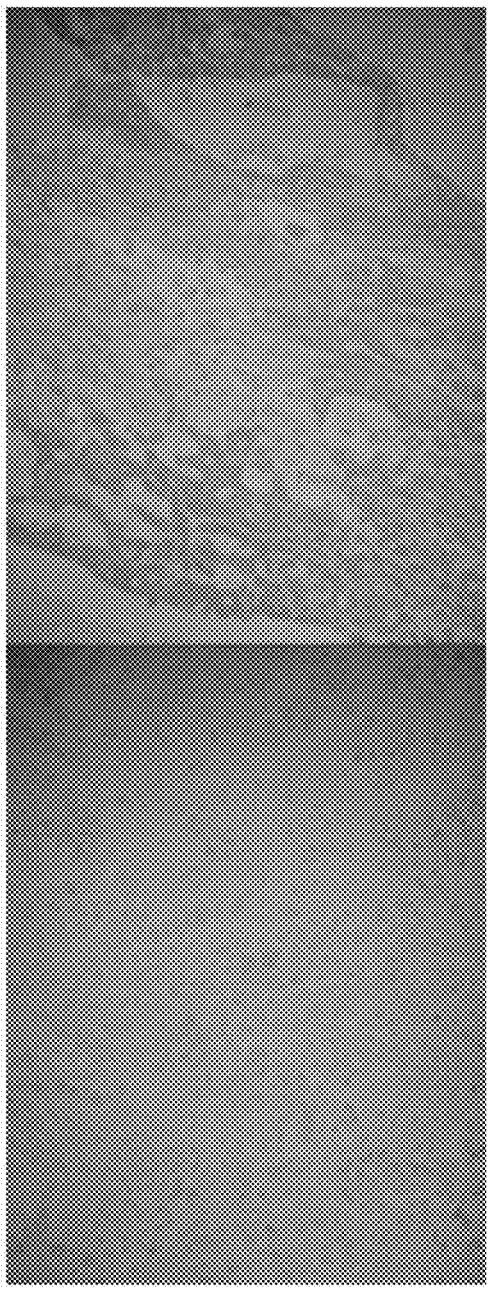
FIG. 5 compares the tissue sections provided in Example 20 of the disclosure.

On Day 41, the tissue sections sampled from the animals in the negative control group and in the treatment group with the test sample prepared in Example 5 were examined, and compared, as shown in FIG. 5.

As can be seen from FIG. 5, the treatment group with the test sample prepared in Example 5 on the right has obviously damaged tumor cells and much darker eosin staining, compared with the negative control group on the left.

Example 21

In Vivo Pharmacodynamics Study on the Selective Inhibition of Recombinant Coxsackie Virus on Solid Tumors The test samples used in this example were prepared and tested according to the protocol described in Example 19.

In this example, three recombinant Coxsackie viruses having a synthetic DNA sequence inserted in their genomes were used as test samples, which were respectively those prepared in Example 1, Example 2, Example 4, and Example 5.

The viruses above were prepared into test samples following the method as described in Example 19.

A subcutaneous A549 cell transplanted tumor model of lung cancer in nude mice was established. 30 tumor-bearing animals having uniform tumor volume were screened. The 30 animals with a tumor volume of 45-72 mm$^3$ (average tumor volume of 57 mm$^3$) were assigned to Groups 1-6 at random. Each group of animals were randomly numbered using Excel software and ranked according to the random number from small to large. There were a total of 6 groups, each group having 5 animals. The groups, dosage and administration mode are shown in Table 4.

TABLE 4

| Group | Agent administered to the animals | Dosage (PFU/kg) | Concentration (PFU/mL) | Administration mode | Volume dosed |
|---|---|---|---|---|---|
| 1 | Saline (negative) | 0.1 mL/10 g | — | Intravenous injection | 0.1 mL/10 g |
| 2 | Cisplatin (positive) | 6 mg/kg | 0.6 mg/mL | Intravenous injection | 0.1 mL/10 g |
| 3 | Example 1 | $6 \times 10^6$ | $6 \times 10^4$ | Intravenous injection | 0.1 mL/10 g |
| 4 | Example 2 | $6 \times 10^5$ | $6 \times 10^3$ | Intravenous injection | 0.1 mL/10 g |
| 5 | Example 4 | $6 \times 10^4$ | $6 \times 10^2$ | Intravenous injection | 0.1 mL/10 g |
| 6 | Example 5 | $6 \times 10^4$ | $6 \times 10^2$ | Intravenous injection | 0.1 mL/10 g |

The animals in Group 2 (Cisplatin) were administered once a week for 4 consecutive weeks. After 1-week observation, the animals were euthanized on Day 48. In the saline group, the animals were administered with saline once a week for 7 consecutive weeks, and the animals were euthanized on Day 48. The animals were observed twice a day during administration to observe the general clinical symptoms of animals, and the body weight and tumor size were measured twice a week.

Figure 6:
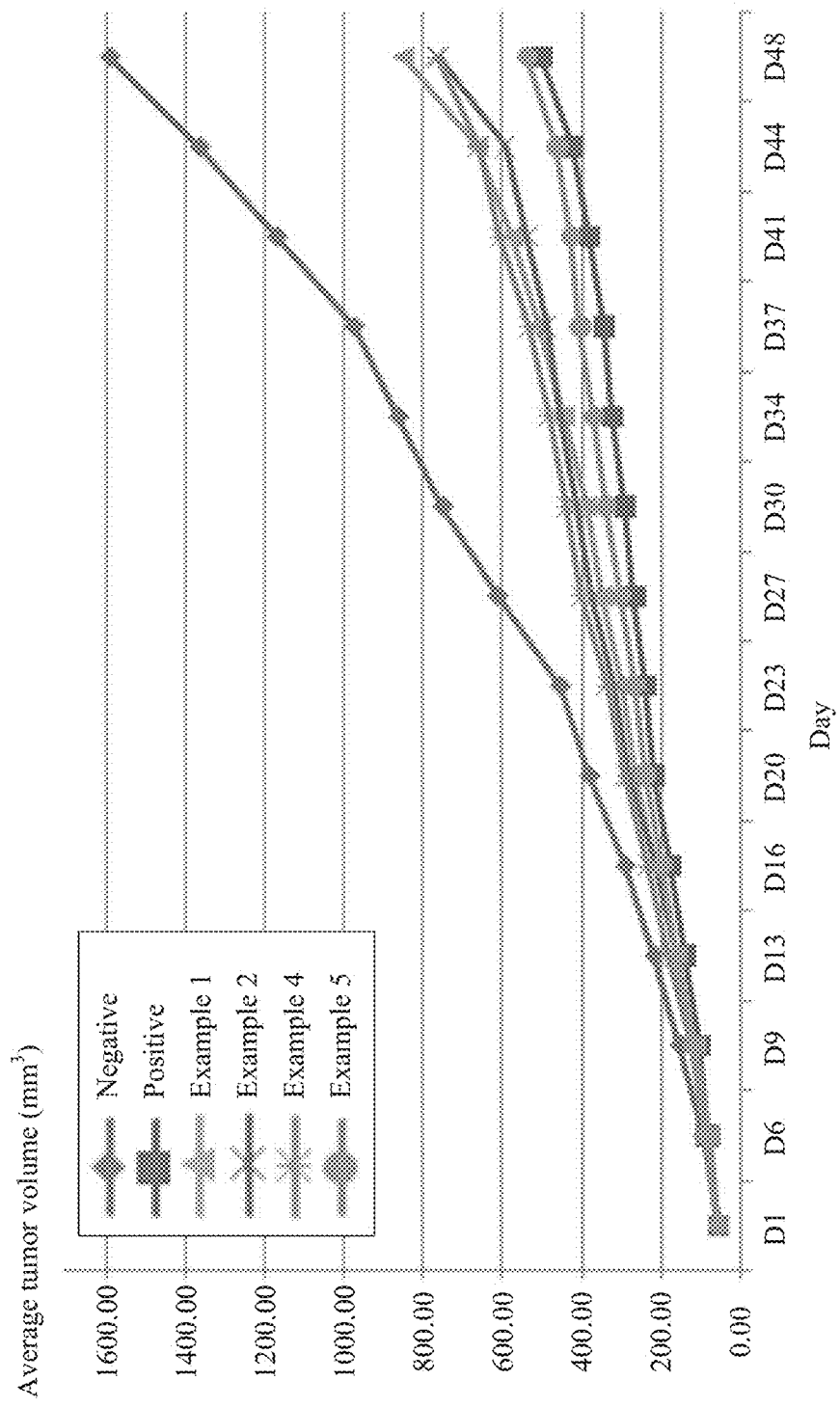
FIG. 6 is a tumor volume curve provided in Example 21 of the disclosure.

Results: Throughout the experiment, the average body weight of the animals is increased, and there is no significant difference between groups (P<0.05). The curve of increase in average tumor volume of the animals in each group with time is shown in FIG. 6.

It can be seen that the test samples prepared in Examples 1, 2, 4, and 5 all have anti-tumor effects, of which the test sample prepared in Example 5 can significantly inhibits tumor growth.

Example 22

In Vivo Pharmacodynamics Study on the Selective Inhibition of Recombinant Coxsackie Virus on Solid Tumors The test samples used in this example were prepared and tested according to the protocol described in Example 19.

In this example, two recombinant Coxsackie viruses having a synthetic DNA sequence inserted in their genomes were used as test samples, which were respectively those prepared in Examples 18, and Example 13.

The viruses above were prepared into test samples following the method as described in Example 19.

A subcutaneous A549 cell transplanted tumor model of lung cancer in nude mice was established. 20 tumor-bearing animals having uniform tumor volume were screened. The 20 animals with a tumor volume of 62-92 mm³ (average tumor volume of 79 mm³) were assigned to Groups 1-4 at random. Each group of animals were randomly numbered using Excel software and ranked according to the random number from small to large. There were a total of 4 groups, each group having 5 animals. The groups, dosage and administration mode are shown in Table 5.

The animals in Group 2 (Cisplatin) were administered once a week for 4 consecutive weeks. After 1-week observation, the animals were euthanized on Day 42. In the saline group, the animals were administered with saline once a week for 6 consecutive weeks, and the animals were euthanized on Day 42. The animals were observed twice a day during administration to observe the general clinical symptoms of animals, and the body weight and tumor size were measured twice a week.

Figure 7:
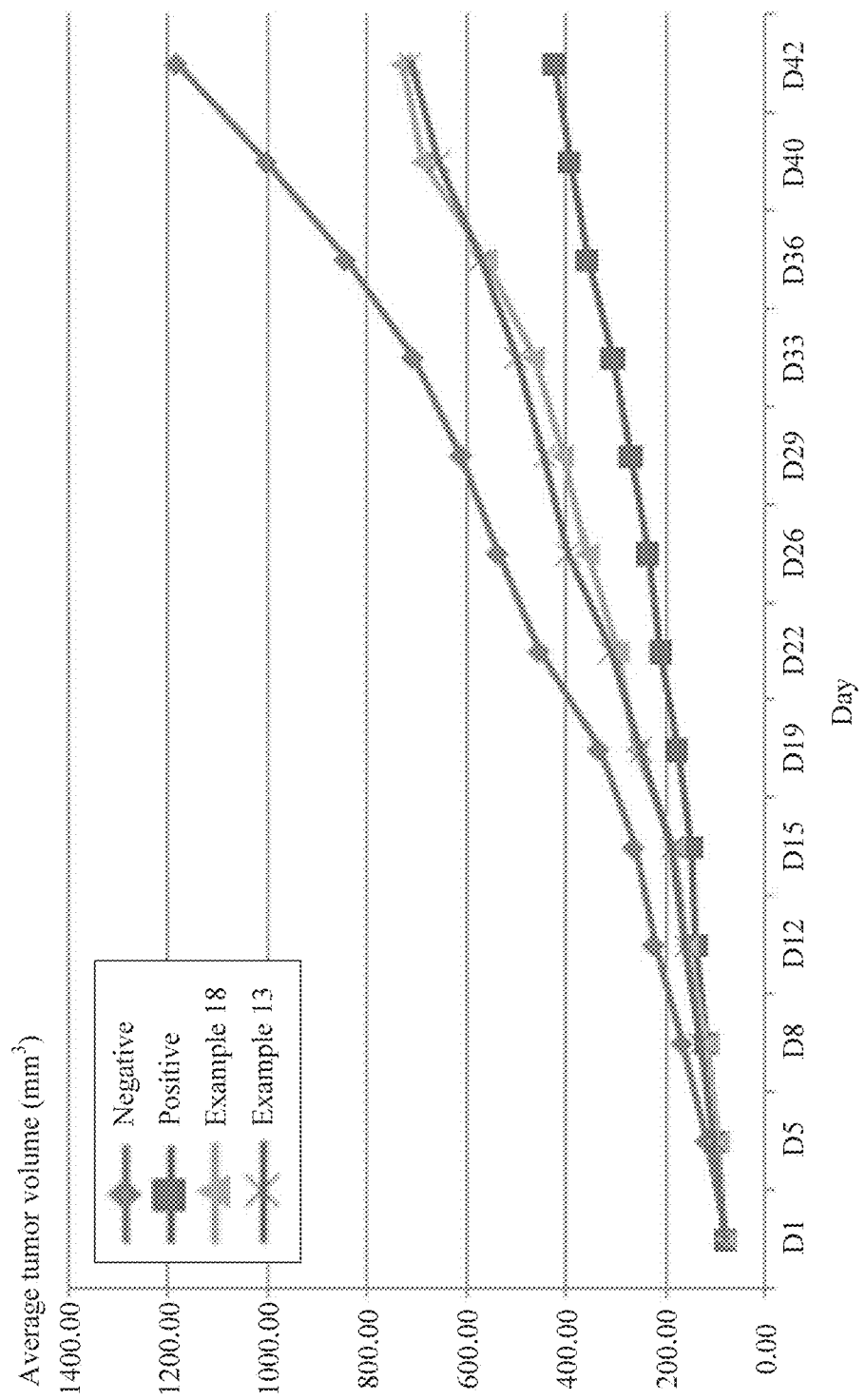
FIG. 7 is a tumor volume curve provided in Example 22 of the disclosure.

Results: Throughout the experiment, the average body weight of the animals is increased, and there is no significant difference between groups (P<0.05). The curve of increase in average tumor volume of the animals in each group with time is shown in FIG. 7.

It can be seen that the test samples prepared in Examples 18 and 13 both have anti-tumor effects.

Example 23

In Vivo Pharmacodynamics Study on the Selective Inhibition of Recombinant Coxsackie Virus on Solid Tumors The test samples used in this example were prepared and tested according to the protocol described in Example 19.

In this example, three recombinant Coxsackie viruses having a synthetic DNA sequence inserted in their genomes were used as test samples, which were respectively those prepared in Examples 8, 9 and 10.

The viruses above were prepared into test samples following the method as described in Example 19.

A subcutaneous A549 cell transplanted tumor model of lung cancer in nude mice was established. 25 tumor-bearing animals having uniform tumor volume were screened. The 25 animals with a tumor volume of 65-90 mm³ average tumor volume of 79 mm³) were assigned to Groups 1-5 at random. Each group of animals were randomly numbered using Excel software and ranked according to the random number from small to large. There were a total of 5 groups, each group having 5 animals. The groups, dosage and administration mode are shown in Table 6.

TABLE 5

| Group | Agent administered to the animals | Dosage (PFU/kg) | Concentration (PFU/mL) | Administration mode | Volume dosed |
|---|---|---|---|---|---|
| 1 | Saline (negative) | 0.1 mL/10 g | — | Intravenous injection | 0.1 mL/10 g |
| 2 | Cisplatin (positive) | 6 mg/kg | 0.6 mg/mL | Intravenous injection | 0.1 mL/10 g |
| 3 | Example 18 | $6 \times 10^6$ | $6 \times 10^4$ | Intravenous injection | 0.1 mL/10 g |
| 4 | Example 13 | $6 \times 10^5$ | $6 \times 10^3$ | Intravenous injection | 0.1 mL/10 g |

TABLE 6

| Group | Agent administered to the animals | Dosage (PFU/kg) | Concentration (PFU/mL) | Administration mode | Volume dosed |
|---|---|---|---|---|---|
| 1 | Saline (negative) | 0.1 mL/10 g | — | Intravenous injection | 0.1 mL/10 g |
| 2 | Cisplatin (positive) | 6 mg/kg | 0.6 mg/mL | Intravenous injection | 0.1 mL/10 g |
| 3 | Example 8 | $6 \times 10^6$ | $6 \times 10^4$ | Intravenous injection | 0.1 mL/10 g |
| 4 | Example 9 | $6 \times 10^5$ | $6 \times 10^3$ | Intravenous injection | 0.1 mL/10 g |
| 5 | Example 10 | $6 \times 10^4$ | $6 \times 10^2$ | Intravenous injection | 0.1 mL/10 g |

The animals in Group 2 (Cisplatin) were administered once a week for 4 consecutive weeks. After 1-week observation, the animals were euthanized on Day 33. In the saline group, the animals were administered with saline once a week for 5 consecutive weeks, and the animals were euthanized on Day 33. The animals were observed twice a day during administration to observe the general clinical symptoms of animals, and the body weight and tumor size were measured twice a week.

Figure 8:
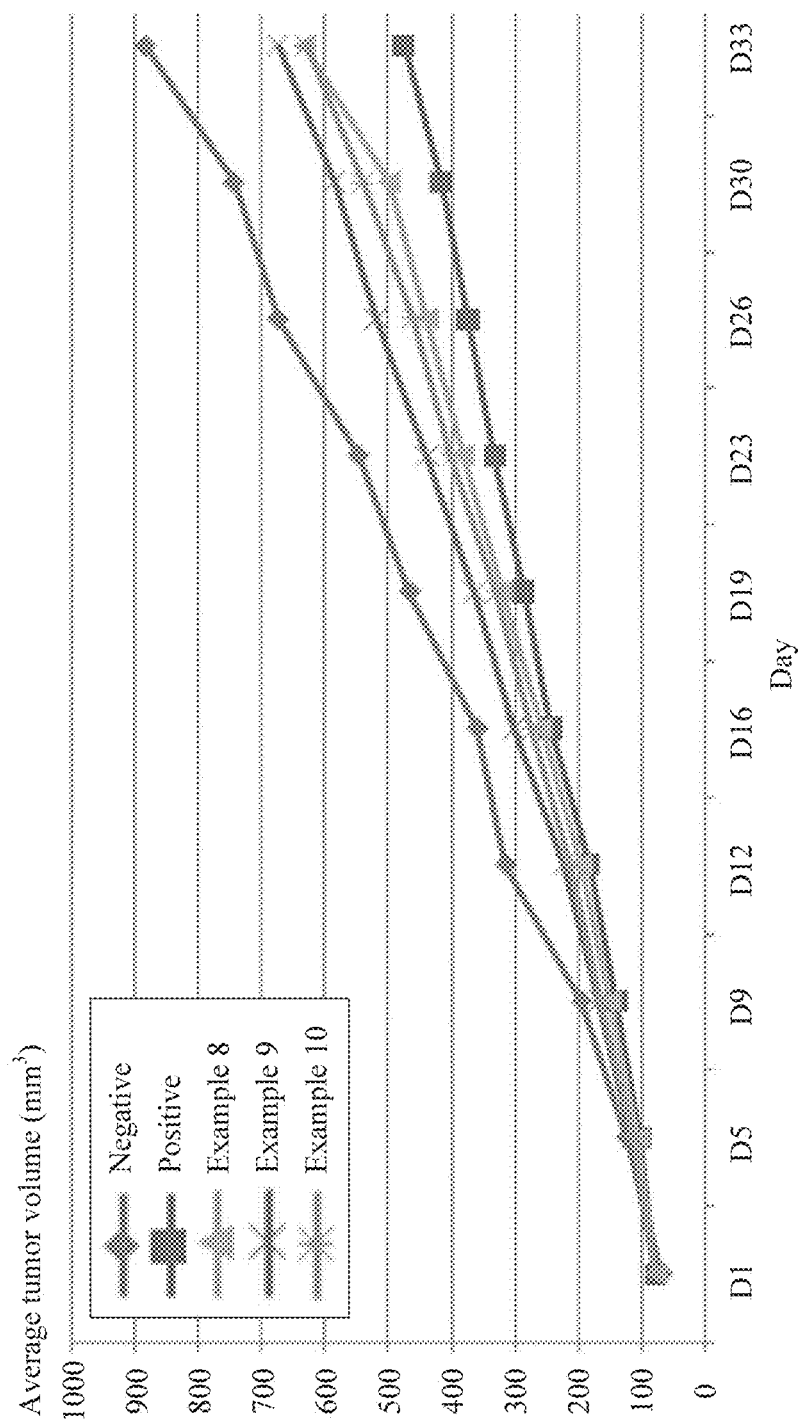
FIG. 8 is a tumor volume curve provided in Example 23 of the disclosure.

Results: Throughout the experiment, the average body weight of the animals is increased, and there is no significant difference between groups (P<0.05). The curve of increase in average tumor volume of the animals in each group with time is shown in FIG. 8.

It can be seen that the test samples prepared in Examples 8, 9 and 10 both have anti-tumor effects.

The test samples prepared in Examples 1 to 18 all have anti-tumor effects, of which the test samples prepared in Examples 5 and 1.4 can significantly inhibits tumor growth.

Example 24

Selective Inhibition of Recombinant Coxsackievirus on Solid Tumors In Vitro

To determine the in vitro cell viability, the human lung cancer cell line A549 was assayed with 3-(4,5-dimethylthiazol-2-yl)-2,5-diphenyl 2H-tetrazolium bromide (MTT). The cells were inoculated in 96-well plates and culture for 24 hours to grow to approximately 80% abundance. The tumor cells were infected with the recombinant CVB3 and the test samples from Example 5, Example 14 and Example 17 at different concentrations (1 PFU/mL, $1 \times 10$ PFU/mL, $1 \times 10^2$ PFU/mL, $1 \times 10^3$ PFU/mL, $1 \times 10^4$ PFU/mL, $1 \times 10^5$ PFU/mL, $1 \times 10^6$ PFU/mL, $1 \times 10^7$ PFU/mL or $1 \times 10^8$ PFU/mL). Normal saline (NS) was used as a negative control and cisplatin was used as a positive control. 72 hours later, the MTT assay was performed according to the manufacturer's protocol (VWR Life Sciences Amresco, Radnor, Pa., USA). The cell culture medium was replaced with 200 μL of MTT (0.5 mg/mL), and the cells were further cultured for 1 h in 10% FBS cell culture medium at 37° C. The supernatants of each group were removed, and 200 μL of dimethyl sulfoxide (DMSO) was added to dissolve the MTT dye in each well. The absorption spectrum was read at a wavelength of 570 nm on a microplate reader. Each treatment was tested with 6 replicates and all assays were in triplicate. The median inhibition concentration ($IC_{50}$) of each group were calculated to be 104797.1, 3290.5, 2051, and 41904.4, respectively.

Figure 9:
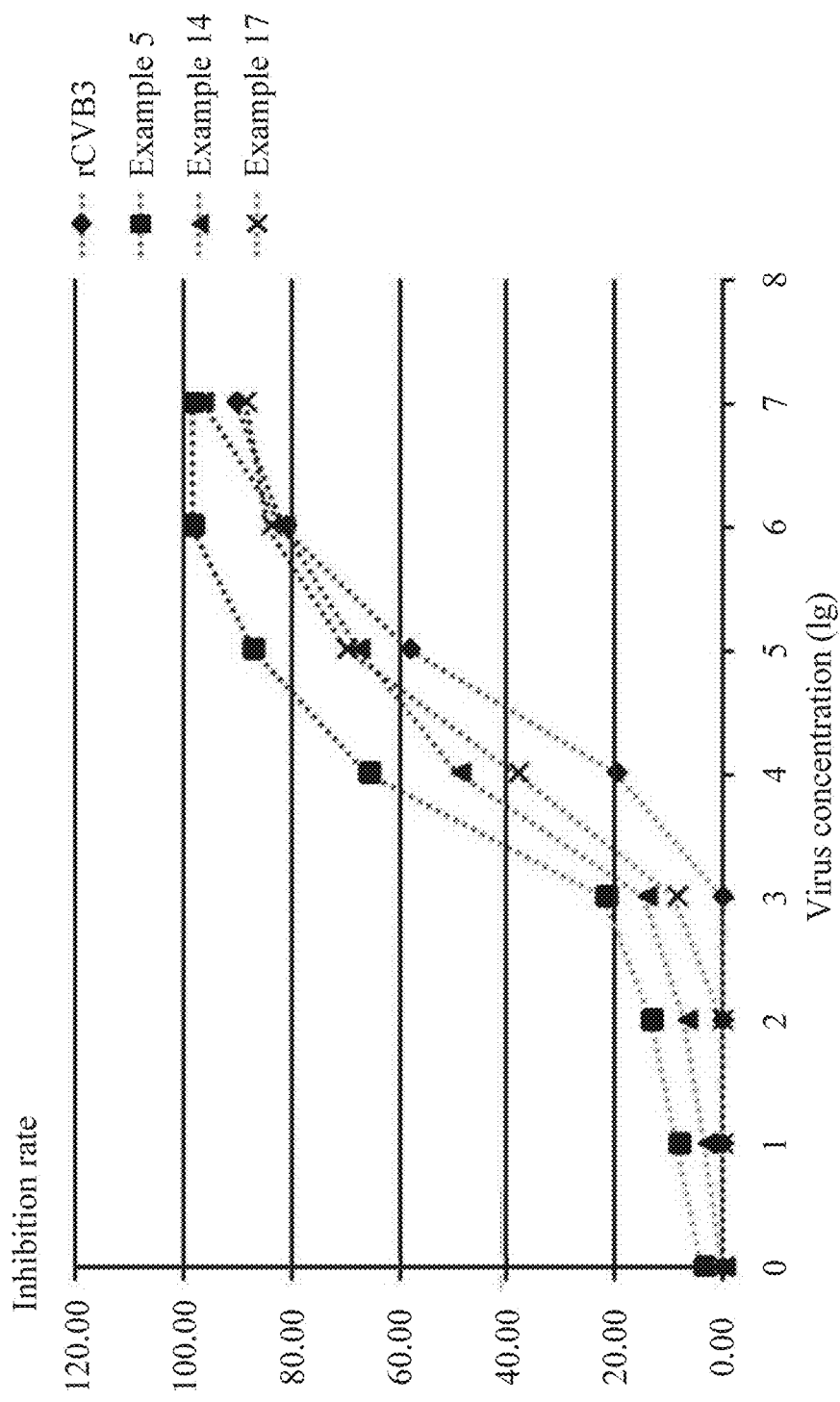
FIG. 9 shows the results of microscopic examination provided in Example 24 of the disclosure.

The inhibition rate of the test samples in each group on the A549 cells in vitro is shown in FIG. 9. FIG. 9 shows the in vitro inhibition rate of recombinant CVB3, samples from Example 5, Example 14, and Example 17 on the A549 cells.

From the experimental results of the cell inhibition rate in vitro, test samples in Example 5 and Example 14 (peptide containing basic amino acids at a content of more than 60%) inhibited tumor cells by more than 95% at a virus concentration of $10^7$. In Example 5, the test sample consists entirely of basic amino acids, and the inhibitory effect is particularly remarkable.

Example 25

Safety Experiment

A toxicity test of cardiomyocytes is conducted to evaluate the safety of the oncolytic virus.

The oncolytic viruses in Example 5 (rCVB3-4pep5) and Example 14 (rCVB3-9pep) were evaluated using rCVB3 and CVB3Nancy strains as positive controls.

Figure 10:
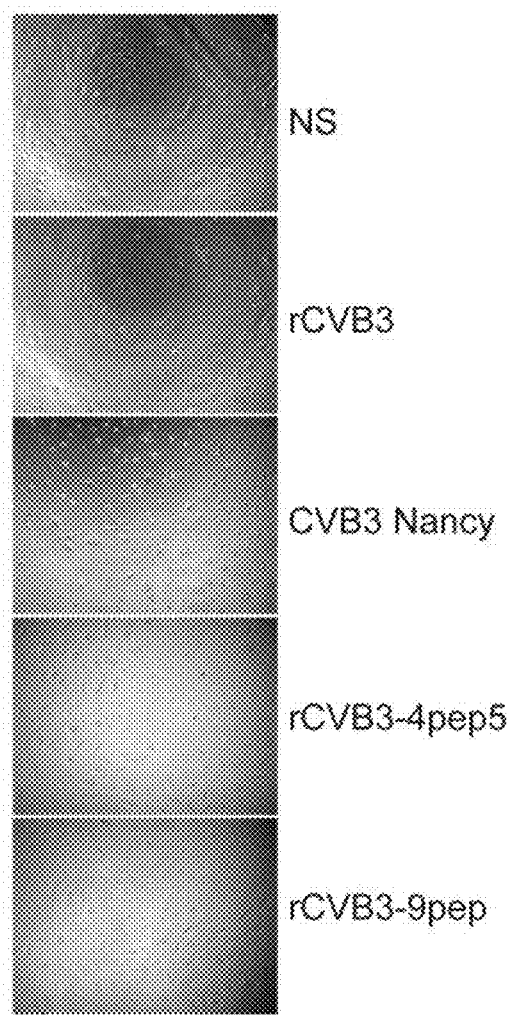
FIG. 10 compares the pH measurements provided in Example 24 of the disclosure.

Cardiomyocyte toxicity testing: infecting the human cardiomyocytes with the viruses of Example 5, Example 14 and the positive control group, respectively (purchased from Suzhou BeiNa Culture Collection Co., Ltd.). The final concentration of the virus was $10^7$ PFU/mL, and normal saline was used as a negative control group. The microscopic examination was performed 72 hours later, and the results are shown in FIG. 10. The CVB3 Nancy strain caused lesions of cardiomyocytes, whereas the three administration groups of rCVB3, Example 5 and Example 14 did not develop lesions.

Figure 11:
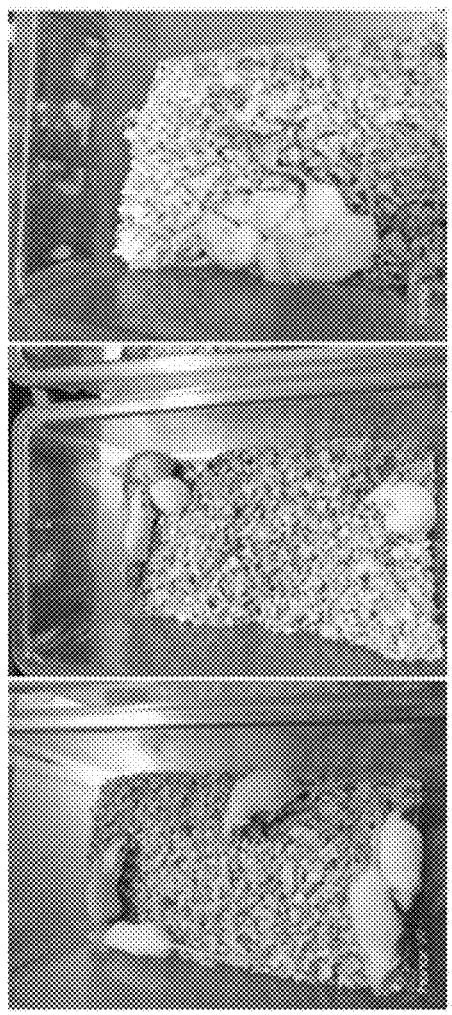
FIG. 11 shows images of the BALB/C mice taken after 6 days of toxicity test n Example 25 of the disclosure.
Figure 11:
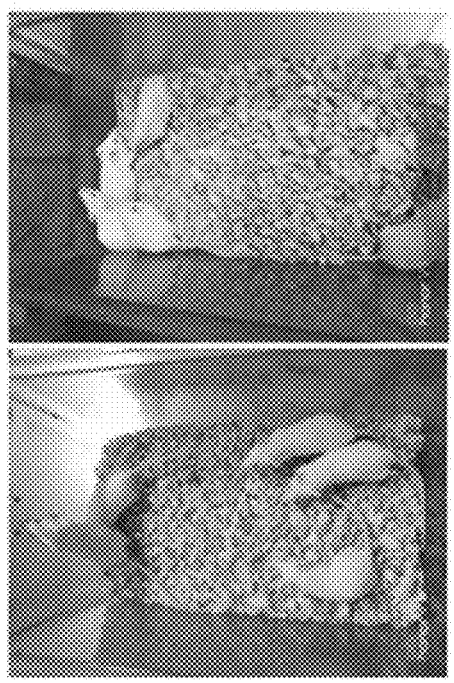

Toxicity testing on BALB/C mice: the viruses of Example 5, Example 14 and the positive control group were injected to the peritoneal cavity of BALB/C mice (license No. 42000600028329), respectively. The mode of administration was $10^8$ PFU/ml, 0.3 mL per mouse per day. Physiological saline was used as a negative control group. The mice were observed every day, and the images on the $6^{th}$ day are shown in FIG. 11. The myocardial tissue of the mice was taken for tissue section, and the results are shown in FIG. 12. The results showed that the mice in the administration group from the CVB3 Nancy strain were in a bad state. The results of the myocardial tissue section showed that the administration group of CVB3 Nancy caused significant myocardial damage, while the administration group of the recombinant CVB3 was normal.

Figure 13:
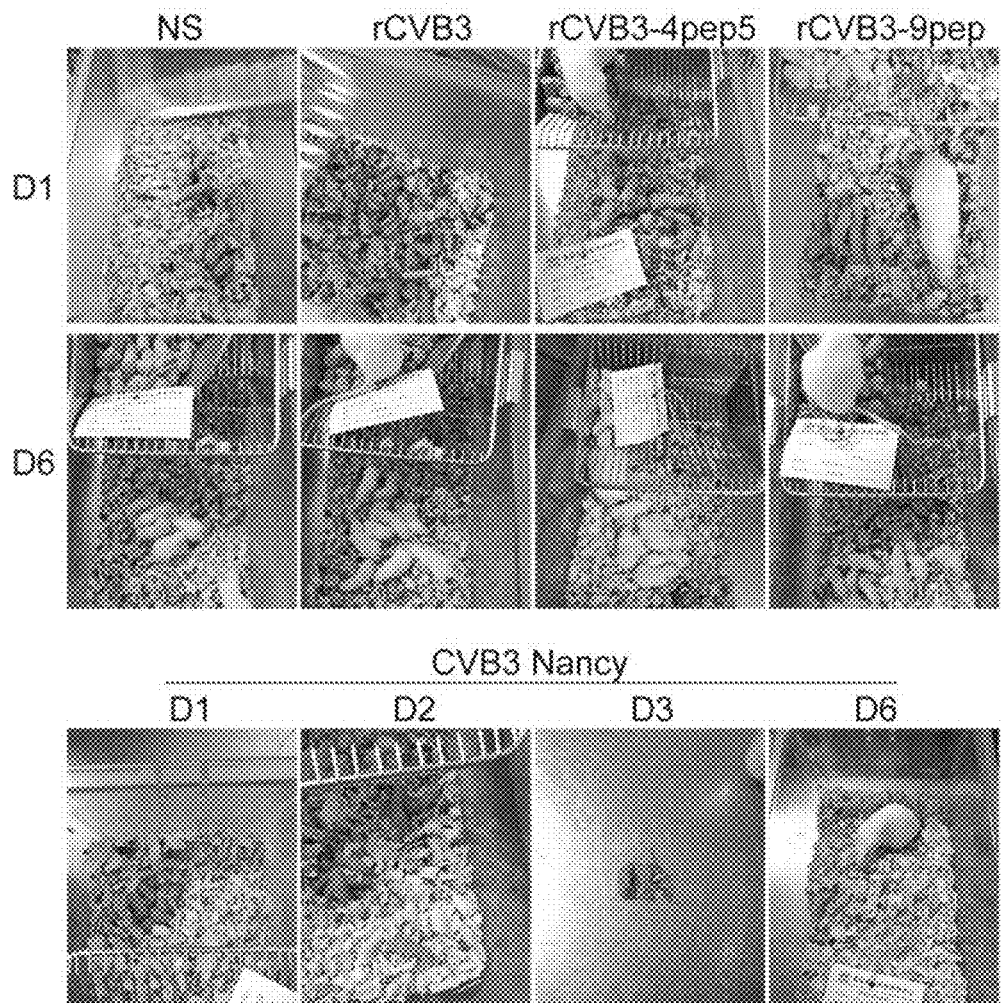
FIG. 13 shows images of suckling mice subject to a toxicity test in Example 25 of the disclosure.

Toxicity testing on suckling mice: the viruses of Example 5, Example 14 and the positive control group were injected into the peritoneal cavity of suckling mice (license No. 42816300002647), respectively. The mode of administration was $10^8$ PFU/ml, 0.3 mL, per mouse per day. Normal saline was used as a negative control group. The mice were observed every day, as shown in FIG. 13. The administration groups of the CVB3 Nancy strain all died on the sixth day, while the administration groups of rCVB3, Example 5, and Example 14 were normal.

The comparative experiments in vitro and in vivo show that rCVB3, Example 5 and Example 14 had significantly weak toxicity compared with CVB3 Nancy strain, indicating that the clinical safety was high.

Example 26

Study on Change of Interstitial pH in Tumors by Recombinant Coxsackie Viruses In this example, two recombinant Coxsackie viruses having a synthetic DNA sequence inserted in their genomes were used as test samples, which were respectively those prepared in Examples 5, and Example 14.

The two viruses were prepared into test samples following the method as described in Example 19.

The two test samples were used to infect Vero cells, respectively. The Vero cells infected with the viruses prepared in Example 5 and Example 14 were designated as 4p5 and 9pep groups, respectively. There was another group of cells that was used as a negative control. Each group of cells included two replicates, which were cultured and tested under the same conditions. 3 hrs after infection, one replicate in each group of cells was stained with Eosin and examined microscopically. The result is as shown in FIG. 14.

Figure 14:
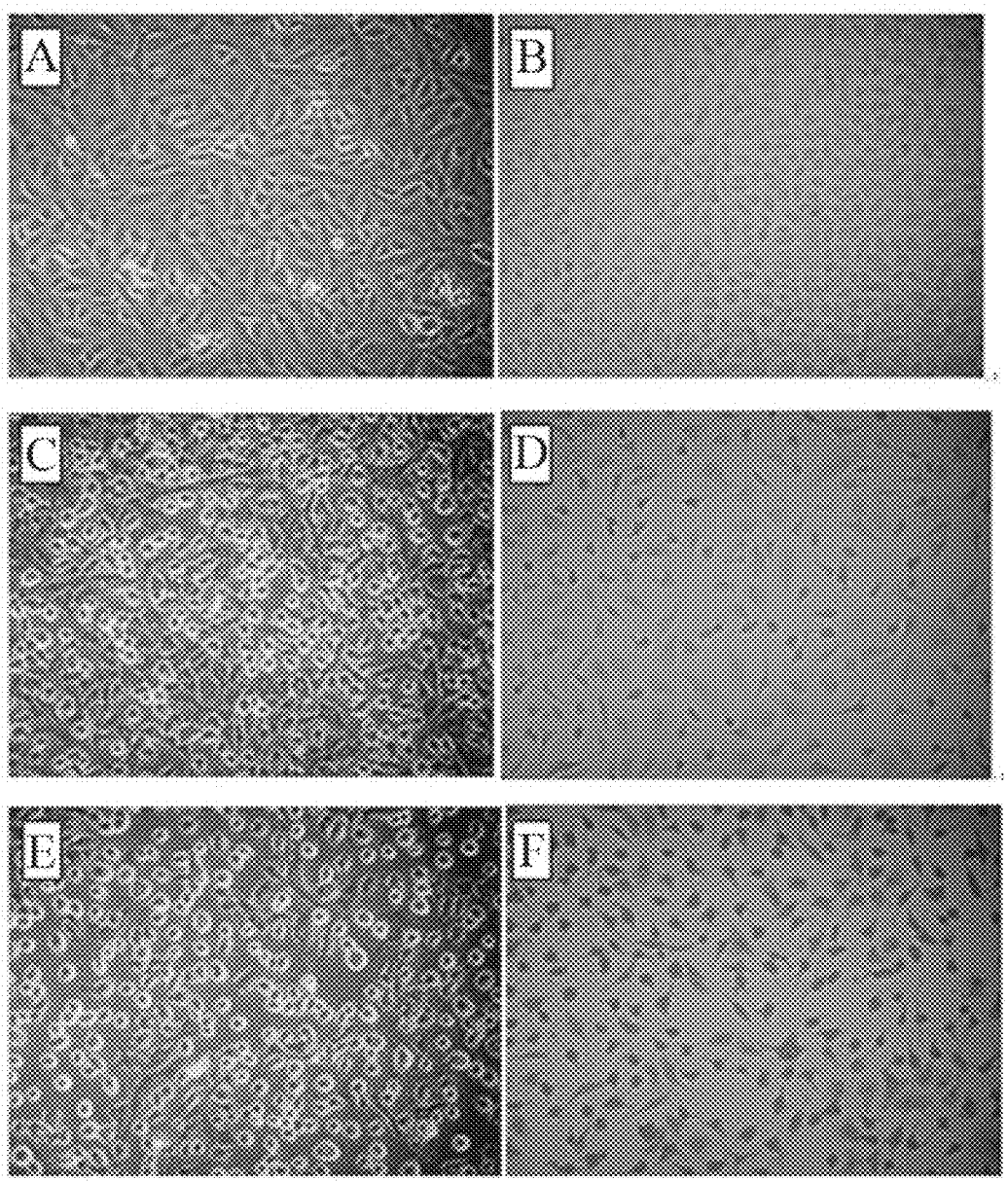
FIG. 14 shows images of microscopic examination according to Example 26 of the disclosure.

As can be seen from FIG. 14, the two group of cells infected with the cDNA of recombinant Coxsackie viruses have obvious pathological changes. It can be seen from the staining results that the infection group is stained darker than the negative control group, indicating that its cytoplasm and interstitial space are more acidophilic.

Figure 15:
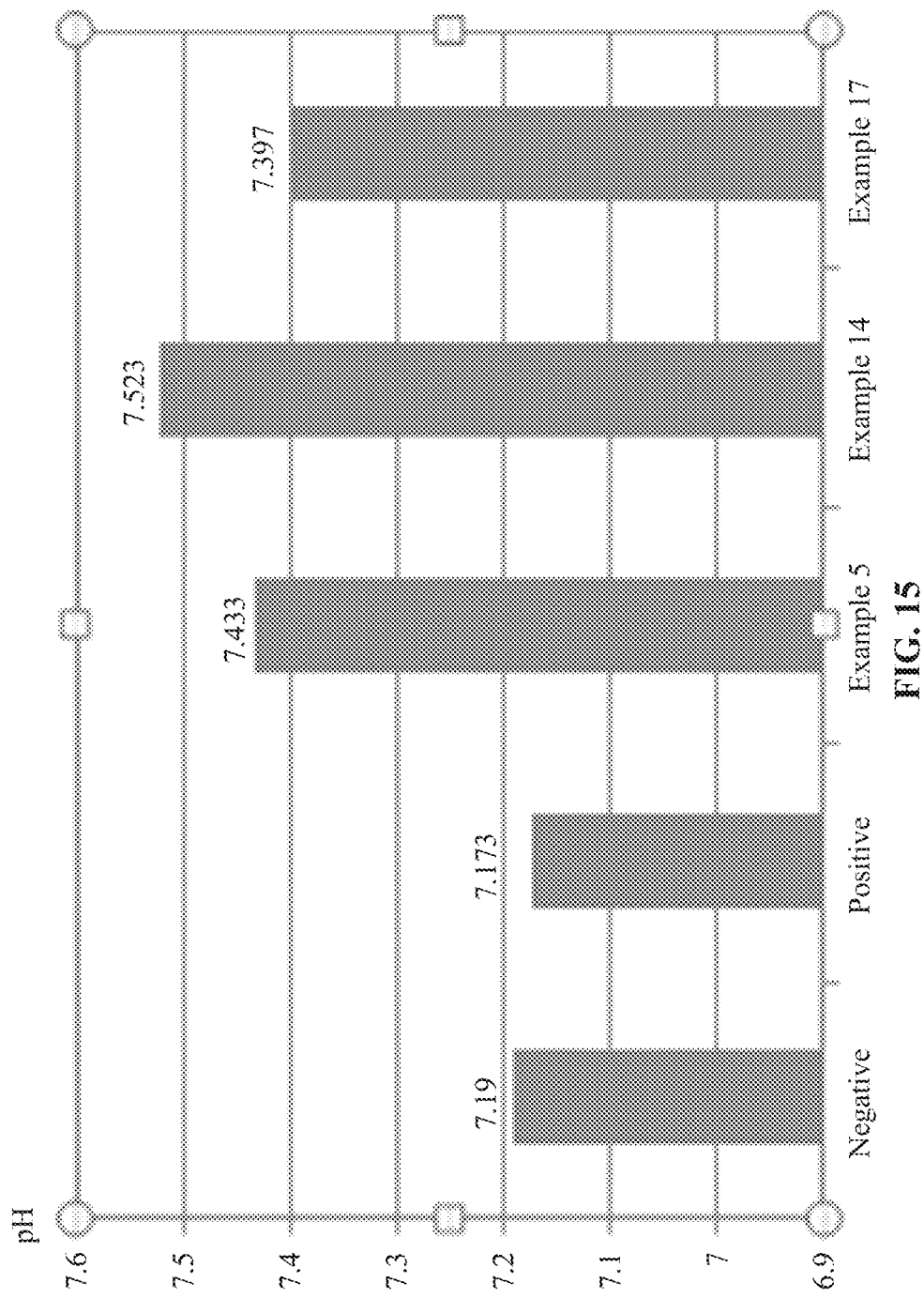
FIG. 15 is a comparison diagram of pH values in Example 26 of the disclosure.

Samples were taken randomly from 3 animals in each test group in Example 20 and the in vivo pH at the tumor site were measured on Day 41 using a Bench-top pH/mV CL-9D02 Meter. The arithmetic mean values of the measurement results for each group are taken, and shown in FIG. 10. The pH value measured with the samples taken from the animals in each test group in Example 20 were found to be increased, by a value of 0.4 to 0.6, as shown in FIG. 15.

Example 27

Inhibition Effect on Different Types of Tumor Cells In Vitro

Figure 16:
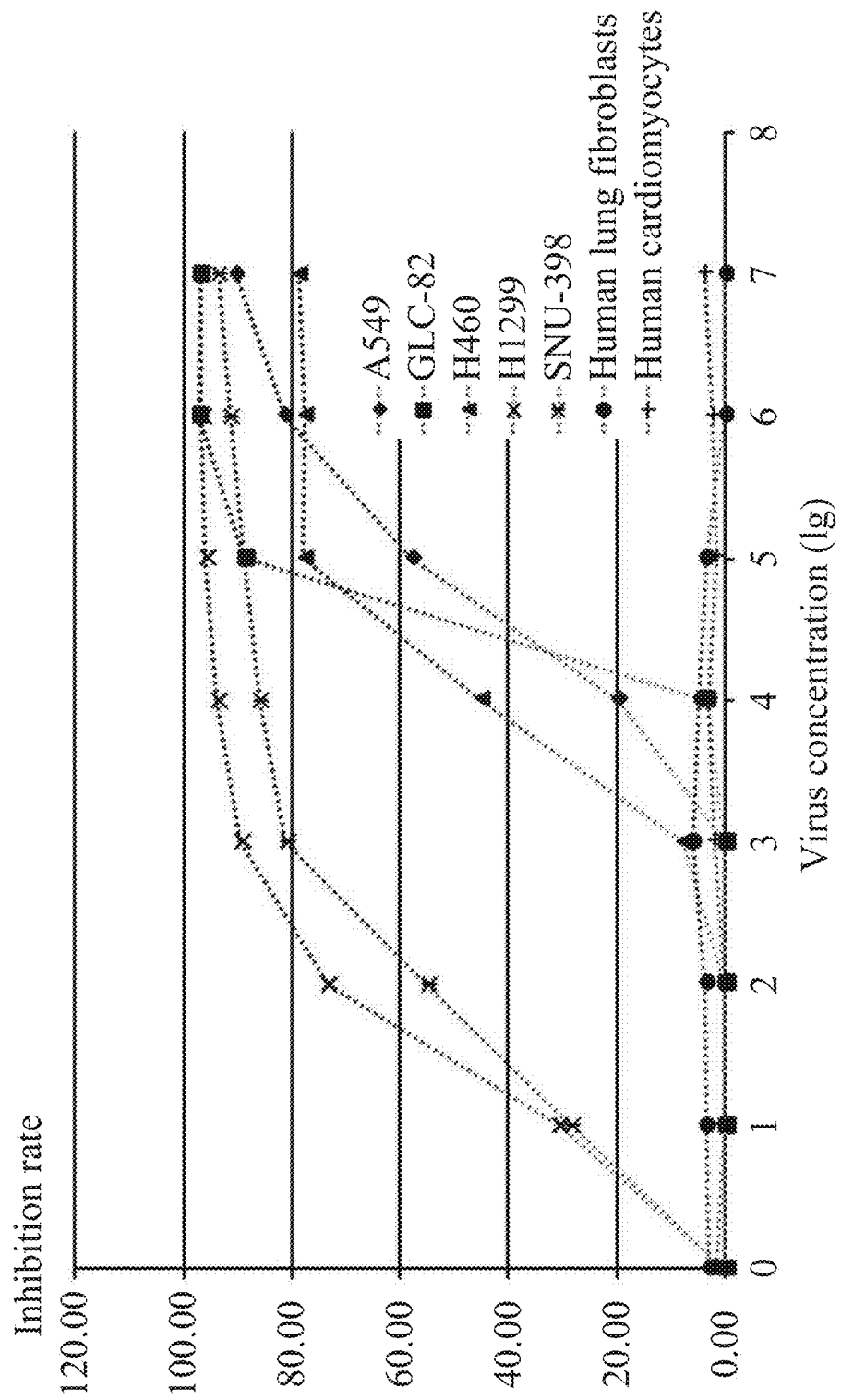
FIG. 16 is a diagram showing the in vitro inhibition on different kinds of tumor cells provided in Example 27 of the disclosure.

To determine the inhibition effect on different types of tumor cells, four human lung cancer cell lines A549, GLC-82, NCI-H460, NCI-H1299, liver cancer SNU-398 and human lung fibroblasts were assayed with 3-(4,5-Dimethyl-thiazol-2-yl)-2,5-diphenyl 2H-tetrazolium bromide (MTT). The cells were inoculated in 96-well plates and culture for 24 hours to grow to approximately 80% abundance. The tumor cells were infected with the recombinant CVB3 at different concentrations (1 PFU/mL, 1×10 PFU/mL, 1×10$^2$ PFU/mL, 1×10$^3$ PFU/mL, 1×10$^4$ PFU/mL, 1×10$^5$ PFU/mL, 1×10$^6$ PFU/mL, 1×10$^7$ PFU/mL or 1×10$^8$ PFU/mL). Normal saline (NS) was used as a negative control and cisplatin was used as a positive control. 72 hours later, the MTT assay was performed according to the manufacturer's protocol (VWR Life Sciences Amresco, Radnor, Pa., USA). The cell culture medium was replaced with 200 μL of MTT (0.5 mg/mL), and the cells were further cultured for 1 h in 10% FBS cell culture medium at 37° C. The supernatants of each group were removed, and 200 μL of dimethyl sulfoxide (DMSO) was added to dissolve the MTT dye in each well. The absorption spectrum was read at a wavelength of 570 nm on a microplate reader. Each treatment was tested with 6 replicates and all assays were in triplicate. The median inhibition concentration (IC$_{50}$) of A549, GLC-82, NCI-H460, NCI-H1299 and SNU-398 were calculated to be 104177.11, 42106.1, 47555.4, 48.0 and 139.1, respectively. The results of the inhibition rate are shown in FIG. 16. FIG. 16 shows the in vitro inhibition rate of recombinant CVB3 on different cells, indicating that the recombinant CVB3 is safe for normal somatic cells.

Experiments show that the oncolytic cells of Example 27 have broad inhibitory effects on different types of lung cancer and liver cancer cells, and have almost no lethality on normal cells.

It will be obvious to those skilled in the art that changes and modifications may be made, and therefore, the aim in the appended claims is to cover all such changes and modifications.

What is claimed is:

1. A recombinant oncolytic virus, comprising: an oncolytic virus genome and an exogenous DNA sequence inserted in the oncolytic virus genome, the exogenous DNA sequence being adapted to express a basic peptide fragment and to increase an environmental pH in a host infected by the recombinant oncolytic virus; wherein:
 - the recombinant oncolytic virus is Coxsackie virus B3 strain, and
 - the basic peptide fragment is Lys-Arg-Trp-His-Lys-Met-Arg-Lys-His (SEQ ID NO: 29).

2. An anti-tumor drug, comprising the recombinant oncolytic virus of claim 1.

3. The drug of claim 2, further comprising a checkpoint inhibitor.

4. A method for treating a malignant tumor, comprising administering the anti-tumor drug of claim 3 intravenously or locally to a patient in need thereof.

5. The method of claim 4, wherein the malignant tumor is a solid tumor.

6. The method of claim 5, wherein the malignant tumor is respiratory tract tumor, gastrointestinal tumor, endocrine tumor, or gynecological tumor.

* * * * *

SEQUENCE LISTING

<160> NUMBER OF SEQ ID NOS: 38

<210> SEQ ID NO 1
<211> LENGTH: 15
<212> TYPE: DNA
<213> ORGANISM: Artificial Sequence
<220> FEATURE:
<223> OTHER INFORMATION: Fully synthetic

<400> SEQUENCE: 1
gcagctcaag aattc 15

<210> SEQ ID NO 2
<211> LENGTH: 24
<212> TYPE: DNA
<213> ORGANISM: Artificial Sequence
<220> FEATURE:
<223> OTHER INFORMATION: Fully synthetic

<400> SEQUENCE: 2
ccctcgaggg aggctttgtt tcaa 24

```
<210> SEQ ID NO 3
<211> LENGTH: 4
<212> TYPE: PRT
<213> ORGANISM: Artificial Sequence
<220> FEATURE:
<223> OTHER INFORMATION: Fully synthetic

<400> SEQUENCE: 3

Arg Lys Arg Lys
1

<210> SEQ ID NO 4
<211> LENGTH: 12
<212> TYPE: DNA
<213> ORGANISM: Artificial Sequence
<220> FEATURE:
<223> OTHER INFORMATION: Fully synthetic

<400> SEQUENCE: 4
aggaagagga ag                                                         12

<210> SEQ ID NO 5
<211> LENGTH: 4
<212> TYPE: PRT
<213> ORGANISM: Artificial Sequence
<220> FEATURE:
<223> OTHER INFORMATION: Fully synthetic

<400> SEQUENCE: 5

Lys Arg Lys Arg
1

<210> SEQ ID NO 6
<211> LENGTH: 12
<212> TYPE: DNA
<213> ORGANISM: Artificial Sequence
<220> FEATURE:
<223> OTHER INFORMATION: Fully synthetic

<400> SEQUENCE: 6
aagaggaaga gg                                                         12

<210> SEQ ID NO 7
<211> LENGTH: 4
<212> TYPE: PRT
<213> ORGANISM: Artificial Sequence
<220> FEATURE:
<223> OTHER INFORMATION: Fully synthetic

<400> SEQUENCE: 7

Arg Arg Lys Lys
1

<210> SEQ ID NO 8
<211> LENGTH: 12
<212> TYPE: DNA
<213> ORGANISM: Artificial Sequence
<220> FEATURE:
<223> OTHER INFORMATION: Fully synthetic

<400> SEQUENCE: 8
aggaggaaga ag                                                         12

<210> SEQ ID NO 9
<211> LENGTH: 4
<212> TYPE: PRT
<213> ORGANISM: Artificial Sequence
```

```
<220> FEATURE:
<223> OTHER INFORMATION: Fully synthetic

<400> SEQUENCE: 9

Lys Lys Arg Arg
1

<210> SEQ ID NO 10
<211> LENGTH: 12
<212> TYPE: DNA
<213> ORGANISM: Artificial Sequence
<220> FEATURE:
<223> OTHER INFORMATION: Fully synthetic

<400> SEQUENCE: 10
aagaagagga gg                                                          12

<210> SEQ ID NO 11
<211> LENGTH: 4
<212> TYPE: PRT
<213> ORGANISM: Artificial Sequence
<220> FEATURE:
<223> OTHER INFORMATION: Fully synthetic

<400> SEQUENCE: 11

Lys Arg Arg Lys
1

<210> SEQ ID NO 12
<211> LENGTH: 12
<212> TYPE: DNA
<213> ORGANISM: Artificial Sequence
<220> FEATURE:
<223> OTHER INFORMATION: Fully synthetic

<400> SEQUENCE: 12
aagaggagga ag                                                          12

<210> SEQ ID NO 13
<211> LENGTH: 4
<212> TYPE: PRT
<213> ORGANISM: Artificial Sequence
<220> FEATURE:
<223> OTHER INFORMATION: Fully synthetic

<400> SEQUENCE: 13

Arg Lys Lys Arg
1

<210> SEQ ID NO 14
<211> LENGTH: 12
<212> TYPE: DNA
<213> ORGANISM: Artificial Sequence
<220> FEATURE:
<223> OTHER INFORMATION: Fully synthetic

<400> SEQUENCE: 14
aggaagaaga gg                                                          12

<210> SEQ ID NO 15
<211> LENGTH: 5
<212> TYPE: PRT
<213> ORGANISM: Artificial Sequence
<220> FEATURE:
<223> OTHER INFORMATION: Fully synthetic

<400> SEQUENCE: 15
```

Arg Arg His Lys Lys
1               5

<210> SEQ ID NO 16
<211> LENGTH: 15
<212> TYPE: DNA
<213> ORGANISM: Artificial Sequence
<220> FEATURE:
<223> OTHER INFORMATION: Fully synthetic

<400> SEQUENCE: 16
aggaggcaca agaag                                                    15

<210> SEQ ID NO 17
<211> LENGTH: 6
<212> TYPE: PRT
<213> ORGANISM: Artificial Sequence
<220> FEATURE:
<223> OTHER INFORMATION: Fully synthetic

<400> SEQUENCE: 17

Lys His Arg Lys His Arg
1               5

<210> SEQ ID NO 18
<211> LENGTH: 18
<212> TYPE: DNA
<213> ORGANISM: Artificial Sequence
<220> FEATURE:
<223> OTHER INFORMATION: Fully synthetic

<400> SEQUENCE: 18
aagcacagga agcacagg                                                 18

<210> SEQ ID NO 19
<211> LENGTH: 6
<212> TYPE: PRT
<213> ORGANISM: Artificial Sequence
<220> FEATURE:
<223> OTHER INFORMATION: Fully synthetic

<400> SEQUENCE: 19

Lys His Arg Cys Lys Pro
1               5

<210> SEQ ID NO 20
<211> LENGTH: 18
<212> TYPE: DNA
<213> ORGANISM: Artificial Sequence
<220> FEATURE:
<223> OTHER INFORMATION: Fully synthetic

<400> SEQUENCE: 20
aagcacaggt gtaagcca                                                 18

<210> SEQ ID NO 21
<211> LENGTH: 6
<212> TYPE: PRT
<213> ORGANISM: Artificial Sequence
<220> FEATURE:
<223> OTHER INFORMATION: Fully synthetic

<400> SEQUENCE: 21

Arg Arg His Lys Met Lys
1               5

<210> SEQ ID NO 22
<211> LENGTH: 18
<212> TYPE: DNA
<213> ORGANISM: Artificial Sequence
<220> FEATURE:
<223> OTHER INFORMATION: Fully synthetic

<400> SEQUENCE: 22
aggaggcaca agatgaag                                                 18

<210> SEQ ID NO 23
<211> LENGTH: 6
<212> TYPE: PRT
<213> ORGANISM: Artificial Sequence
<220> FEATURE:
<223> OTHER INFORMATION: Fully synthetic

<400> SEQUENCE: 23

His Arg Lys Cys Arg Lys
1               5

<210> SEQ ID NO 24
<211> LENGTH: 18
<212> TYPE: DNA
<213> ORGANISM: Artificial Sequence
<220> FEATURE:
<223> OTHER INFORMATION: Fully synthetic

<400> SEQUENCE: 24
cacaggaagt gtaggaag                                                 18

<210> SEQ ID NO 25
<211> LENGTH: 7
<212> TYPE: PRT
<213> ORGANISM: Artificial Sequence
<220> FEATURE:
<223> OTHER INFORMATION: Fully synthetic

<400> SEQUENCE: 25

Lys Arg Trp Arg Lys His Arg
1               5

<210> SEQ ID NO 26
<211> LENGTH: 21
<212> TYPE: DNA
<213> ORGANISM: Artificial Sequence
<220> FEATURE:
<223> OTHER INFORMATION: Fully synthetic

<400> SEQUENCE: 26
aagaggtgga ggaagcacag g                                             21

<210> SEQ ID NO 27
<211> LENGTH: 8
<212> TYPE: PRT
<213> ORGANISM: Artificial Sequence
<220> FEATURE:
<223> OTHER INFORMATION: Fully synthetic

<400> SEQUENCE: 27

His Lys Gly Arg Lys Cys Arg Val
1               5

<210> SEQ ID NO 28
<211> LENGTH: 24
<212> TYPE: DNA

```
<213> ORGANISM: Artificial Sequence
<220> FEATURE:
<223> OTHER INFORMATION: Fully synthetic

<400> SEQUENCE: 28
cacaagggaa ggaagtgtag ggtg                                          24

<210> SEQ ID NO 29
<211> LENGTH: 9
<212> TYPE: PRT
<213> ORGANISM: Artificial Sequence
<220> FEATURE:
<223> OTHER INFORMATION: Fully synthetic

<400> SEQUENCE: 29

Lys Arg Trp His Lys Met Arg Lys His
1               5

<210> SEQ ID NO 30
<211> LENGTH: 27
<212> TYPE: DNA
<213> ORGANISM: Artificial Sequence
<220> FEATURE:
<223> OTHER INFORMATION: Fully synthetic

<400> SEQUENCE: 30
aagaggtggc acaagatgag gaagcac                                       27

<210> SEQ ID NO 31
<211> LENGTH: 9
<212> TYPE: PRT
<213> ORGANISM: Artificial Sequence
<220> FEATURE:
<223> OTHER INFORMATION: Fully synthetic

<400> SEQUENCE: 31

His Phe Trp Arg Gln Cys Ala Met Lys
1               5

<210> SEQ ID NO 32
<211> LENGTH: 27
<212> TYPE: DNA
<213> ORGANISM: Artificial Sequence
<220> FEATURE:
<223> OTHER INFORMATION: Fully synthetic

<400> SEQUENCE: 32
cacttctggc gacaatgtgc tatgaag                                       27

<210> SEQ ID NO 33
<211> LENGTH: 9
<212> TYPE: PRT
<213> ORGANISM: Artificial Sequence
<220> FEATURE:
<223> OTHER INFORMATION: Fully synthetic

<400> SEQUENCE: 33

Tyr Phe Pro Arg His Gln Lys Trp Lys
1               5

<210> SEQ ID NO 34
<211> LENGTH: 27
<212> TYPE: DNA
<213> ORGANISM: Artificial Sequence
<220> FEATURE:
<223> OTHER INFORMATION: Fully synthetic
```

-continued

```
<400> SEQUENCE: 34
tacttccctc gtcatcaaaa gtggaag                                        27

<210> SEQ ID NO 35
<211> LENGTH: 9
<212> TYPE: PRT
<213> ORGANISM: Artificial Sequence
<220> FEATURE:
<223> OTHER INFORMATION: Fully synthetic

<400> SEQUENCE: 35

Trp Lys Tyr Arg Gln Ile Ser Thr Cys
1               5

<210> SEQ ID NO 36
<211> LENGTH: 27
<212> TYPE: DNA
<213> ORGANISM: Artificial Sequence
<220> FEATURE:
<223> OTHER INFORMATION: Fully synthetic

<400> SEQUENCE: 36
tggaagtacc gccagatcag cacctgc                                        27

<210> SEQ ID NO 37
<211> LENGTH: 10
<212> TYPE: PRT
<213> ORGANISM: Artificial Sequence
<220> FEATURE:
<223> OTHER INFORMATION: Fully synthetic

<400> SEQUENCE: 37

Arg Lys His Lys Met Arg Lys Cys His Lys
1               5                   10

<210> SEQ ID NO 38
<211> LENGTH: 30
<212> TYPE: DNA
<213> ORGANISM: Artificial Sequence
<220> FEATURE:
<223> OTHER INFORMATION: Fully synthetic

<400> SEQUENCE: 38
aggaagcaca agatgaggaa gtgtcacaag                                     30
```